United States Patent [19]

Babaian et al.

[11] Patent Number: 4,921,695
[45] Date of Patent: May 1, 1990

[54] ANTIANGINAL PLATE FOR TREATING ISCHEMIC HEART DISEASE

[76] Inventors: Eduard A. Babaian, ulitsa Novatorov 36, Korpus 9, kv. 12; Galina A. Gerasimova, ulitsa Shepilovskaya 36, Korpus 2, kv. 131; Anatoly B. Davydov, ulitsa Krasny Kazanets 19, Korpus 1, kv. 283; Rustam I. Utyamyshev, Prospekt Mira 118, kv. 222; Gennady L. Khromov, 2 Frunzenskaya ulitsa 10, kv. 100; Vladimir I. Metelitsa, Khimki, Jubileiny prospekt, 35, kv. 186; Anatoly M. Vikhert, ulitsa Burdenko 11, kv. 8-a; Konstantin L. Savvateev, ulitsa Chusovskaya 15, kv. 75; Vladimir K. Piotrovsky, ulitsa Akademika Skryabina, 3, korpus 1, kv. 59; Elizaveta B. Novikova, Petrovsko-Razumovskaya alleya 18, kv. 25, all of, Moscow, U.S.S.R.

[21] Appl. No.: 320,976

[22] Filed: Mar. 9, 1989

Related U.S. Application Data

[60] Division of Ser. No. 50,526, May 13, 1987, Pat. No. 4,842,854, which is a continuation-in-part of Ser. No. 799,210, Nov. 19, 1985, Pat. No. 4,713,239, which is a continuation of Ser. No. 42,874, May 29, 1979, abandoned.

[51] Int. Cl.$^5$ .................. A61K 9/20; A61K 31/79
[52] U.S. Cl. ...................... 424/81; 424/78; 424/435
[58] Field of Search .............. 424/78, 81, 435

[56] References Cited

U.S. PATENT DOCUMENTS

| 3,429,308 | 2/1969 | Russell | 424/14 |
|---|---|---|---|
| 3,444,858 | 5/1969 | Russell | 424/28 |
| 3,870,790 | 3/1975 | Lowey et al. | 424/19 |
| 4,059,686 | 11/1977 | Tanaka et al. | 424/19 |
| 4,226,848 | 10/1980 | Nagai et al. | 424/19 |
| 4,529,589 | 7/1985 | Davydov et al. | 424/81 |
| 4,713,239 | 12/1987 | Babian et al. | 424/81 |

Primary Examiner—Shep K. Rose
Attorney, Agent, or Firm—Burgess, Ryan & Wayne

[57] ABSTRACT

An antianginal composition in the form of a plate is provided for treating ischemic heart disease and is comprised of a biologically soluble and resolvable film and an antianginal coronary vasodilating nitrate. This film is placed buccally on the gum or mouth mucosa for rapid arresting or prevention of angina pectoris attacks.

The antianginal film is in the form of a plate, 0.1 to 1.5 mm thick, consisting of a biologically soluble and resolvable carrier. Preferably, the film is comprised of a homoploymer of acrylamide or vinylpyrrolidone, or a copolymer thereof with acrylate, containing from 99 to 70 percent by weight of acrylamide with vinylpyrrolidone and from 1 to 30 percent by weight of acrylate having a molecular mass from 50,000 to 1,000,000, and the active principle having antianginal action, the components being taken in the following proportions, in percent by weight:

| active substance having antianginal action | 3.0–30.0 |
|---|---|
| biologically soluble and resolvable carrier | 70.0–97.0 |

7 Claims, 3 Drawing Sheets

ANTIANGINAL PLATE FOR TREATING ISCHEMIC HEART DISEASE

RELATED APPLICATION

This is a division of application Ser. No. 050,526, filed May 13, 1987, now U.S. Pat. No. 4,842,854, which is a Continuation-in-Part of U.S. Pat. No. 799,210 filed Nov. 19, 1985, now U.S. Pat. No. 4,713,239 issued 12/15/87, which is a continuation of U.S. Pat. No. 042,874 filed May 29, 1979, now abandoned.

FIELD OF THE INVENTION

This invention relates to pharmacy, and more particularly it relates to a new medicinal form, a medicinal plate having antianginal action, and the method of treating ischemic heart disease. Such antianginal plates are used in cardiology to treat ischemic heart disease.

BACKGROUND OF THE INVENTION

Known in the prior art are antianginal preparations used to arrest attacks of angina pectoris containing active substances such as glycerol trinitrate, isosorbide dinitrate, pentaerythritol tetranitrate, and others.

In addition to said active substances, these medicinal preparations contain an inert carrier which is resolved in liquid media of the body. For example, used in the prior art are granules of glycerol trinitrate containing sugar, starch, and other substances as filling materials (Soviet State Pharmacopoeia, 10th edition).

A disadvantage of the known medicinal preparations containing readily soluble substances such as sugar as a filling material, is their low stability in storage and lack of prolonged action.

Also known in the prior art are tablets of glycerol trinitrate, prepared by the microcapsulation method (Sustac Nitrong) wherein the microcapsules perform the function of the carrier material which is a derivative of cellulose such as methyl cellulose, ethyl cellulose, acetyl cellulose, cellulose acetophthalate, etc.

Medicinal preparations enclosed in microcapsules start exerting their medicinal action at delayed (to 60 minutes) terms, and this makes it impossible to use them for rapid arresting of angina pectoris attacks.

Another disadvantage of capsuled preparations is the relative complexity of their manufacture.

Known widely in the prior art are antianginal preparations manufactured in the form of tablets and dragees. These also include multi-coated pills containing synthetic polymers such as polyvinyl alcohol, and a copolymer of polyvinyl alcohol and vinyl acetate, as resolvable carrier material. Synthetic polymers are used to coat tablets or granules so that the rate of liberation of the active principle could be controlled. (French Pat. No. 2,326,933; U.S. Pat. No. 4,012,498).

Also known in the prior art are antianginal preparations in the form of chewing gum containing the active principle and various additives. The base material used in these preparations are polyacrylate polymers (U.S. Pat. No. 3,594,470).

The disadvantages of the known medicinal preparations in the form of tablets pressed with powdered synthetic polymers, and also enclosed in coats of such polymers, is that they can be improperly administered (especially by children who can chew them before swallowing) and hence produce undesirable side effects due to rapid uncontrolled absorption into the body.

The method of treating with such medicinal preparations involves the patient swallowing the medicine (peroral administration), or placing it under the tongue until it fully resolves (sublingual administration) or chewing the gum to ensure gradual administration of the medicine with saliva. In all these administration methods, the active principle penetrates the alimentary tract where it is dissolved, absorbed through the mucosa, and delivered first to the liver and then to the blood circulating system (Petkov, V., "Medicine, Body, Pharmacological Effect", Medicina i Fizkultura Sofia, 1974).

The general pharmacological disadvantage inherent in all known medicinal antianginal preparations is that when the preparations enter the alimentary tract, and later the liver, the liberated active substance is partially inactivated by the enzymatic systems in the body. The degree of inactivation of the preparations depends on specific characteristics of the living body and its physiological state which, in general, makes it impossible to dose the medicinal preparation individually so as to ensure its optimum effect.

U.S. Pat. No. 3,429,308, which issued to H.S. Russell on Feb. 25, 1969, discloses a method for administering drugs from a vehicle adhering by suction to the parabuccal cavity mucous membrane. The vehicle used to administer the drug is a gelatinous material and is configured to have a generally concave depression on its major surface and is relatively thin so as to be of a substantially flexible but resilient nature. The vehicle may also be a gelatinous material based on the alginates or a resin-based material. When a drug containing vehicle is introduced into the parabuccal cavity, it becomes adhered to the mucous membrane by virtue of a suction effect afforded by means of the concave depression. The vehicle can be in the form of a lozenge and when it is desired to administer the drug, the lozenge is merely moistened on the concave side and pressed firmly against the gum of the upper jaw of the patient. It is indicated in the patent that by firmly pressing the lozenge against the mucous membrane of the parabuccal cavity, at least some of the air is dispelled from the depression to produce a suction effect, whereby the lozenge adheres to the surface and the drug is absorbed into the mucous membrane.

Although the reference does not indicate how quickly absorption begins, it states at column 4, lines 31 et seq. that absorption is allowed to continue until the desired effect of the drug is obtained. No indication is given as to the period of time during which absorption of the drug continues.

A wide variety of drugs are disclosed which can be contained in the vehicle and include, hormones, local anesthetics, sympathomimetic amines, vasodilators, cardiovascular reactants such as glyceryl trinitrate, muscle relaxants, antihistamines, and the like.

It is indicated in this patent that the invention operates as a convenient vehicle for administering drugs which avoids known disadvantages and yet has the advantage of permitting substantially instantaneous discontinuance of administration and comprehends a vehicle for administering a drug in the form of a thin body of resilient gelatinous material having a concave depression on at least one of the major surfaces thereof and being of such shape as to enable it to be introduced into the parabuccal cavity for adherence by suction to the mucous membrane by reason of the concave depression, and wherein the material of the body is impregnated with a drug which is effective when absorbed through the mucous membrane, which drug may be of a nature such that, if administered by swallowing, it would be subject to destruction or inactivation by stomach or intestine saliva or fluid, or would cause unwanted side effects, or would require massive overdoses.

The vehicle is made by preparing a liquid solution or melt of a gelatinous material, impregnating the solution or melt with a drug, preferably of hormonal nature which is effective when absorbed through the mucous membrane of the parabuccal cavity, and forming the impregnated solution or melt into the vehicle.

The material, in main part, is a gelatine which acts as a diluent for a water soluble drug which is dissolved in the gelatine prior to the formation of the lozenge. Contrarywise, the active ingredient may be dissolved in water or other diluent and added to the lozenge by injection, soaking, spraying, dipping or any other method once the lozenge is made.

Other glyco-gelatine based mixtures, or a gelatinous material based on the alginates, or other suitable, for instance, resin-based materials may be used. However, it is indicated that a material based on gelatine is preferred.

The vehicle offers the advantage that it does not fragment so that it may be easily removed when a sufficient amount of the drug has been absorbed. Accordingly, the vehicle is particularly suitable for administering drugs which produce easily identifiable signs of sufficient absorption thereof. Since the vehicle adheres to the gum and also abuts the adjacent membrane of the lip, even to the extent of adhering to the latter, very little of the drug is washed away or inactivated by any saliva present in the patient's mouth.

As indicated above, the vehicle used in the medication is based on gelatin or its analogs (Column 3, line 23). There is no indication of other polymeric materials being used in preparing the medications. An obvious disadvantage of gelatin and its analogs when used in controlled release drugs, is the insolubility of gelatin in saliva and the impossibility of homogeneous systems with a controlled hydrophilic-hydrophobic balance predetermining the drug release rate into the mucous surfaces being developed. The medication must be removed from the mouth cavity at the end of drug action, as taught in claim 2, which makes individual and precise dosing of the drug difficult.

Another reference, U.S. Pat. No. 3,444,858 also issued to H. S. Russell on May 20, 1969, is directed to a resiliently flexible gelatinous material in the form of a strip which can be inserted into the buccal sulcus and which contains an absorbable drug. It is indicated in this patent that the invention also provides a method of making a vehicle comprising the steps of preparing a liquid solution or melt of a gelatinous material, impregnating the solution or melt with said drug and forming the impregnated solution or melt into the vehicle.

The vehicle is preferably in a form of glycol-gelatine which is sufficiently firm and solid to be resilient and is conveniently in the form of an extrusion of rectangular or oval cross section.

In a preferred form, the vehicle is impregnated with a drug of very potent nature as such drugs are usually effective even when administered in very small amounts, e.g., in doses of a fraction of a milligram.

The vehicle may be prepared by any suitable means and from any suitable flexible or gelatinous material and, in the instance wherein the material comprises mainly glycol-gelatine, various plasticizers and diluents may be incorporated, not only to improve and/or vary the qualities of the vehicle, but also to facilitate the production thereof, and the incorporation of the drug or drugs.

The strip is formed at intervals, with pairs of transverse depressions in opposite major faces thereof so as to divide the strip into a plurality of sections which are each connected to the next adjacent sections by comparatively weak ligaments.

The purpose of these ligaments is to enable the strip to be torn or otherwise divided up into individual lengths each of which consists of one or a desired number of the sections.

In this manner, the desired dosage of drug can be administered by use of an appropriate number of sections. The reference is silent as to the duration of effect or how quickly the drug is absorbed.

It is also indicated in the patent that while glycol based materials are preferred, the strips can be made from other materials. Also, as in the earlier cited Russell patent, a variety of drugs can be incorporated into the vehicles of this patent.

Solid pharmaceutical formations containing hydroxypropyl methyl cellulose are disclosed in U.S. Pat. No. 3,870,790, which issued March 11, 1975 to Hans Lowey and is assigned to Forest Laboratories, Inc. of New York, and are indicated to be useful as long-acting compositions for the administration of transmucosally absorbed therapeutic agents.

In general, the long acting carrier products of the invention are produced by combining the appropriate amount of active ingredient into the shape of troches, lozenges, tablets or suppositories with a mixture of from about 100–80% by weight of hydroxypropylmethylcellulose and from about 0–20% by weight of ethylcellulose. The produce can also contain adjuvants such as a synthetic sweetening agent and the like.

When used as a lozenge, release through the action of the saliva is continuous and the active ingredient then passes through the gastro-intestinal tract into the blood stream. However, when the composition is positioned in the buccal pouch, absorption of the active ingredient takes place through the mucosa membrane lining the pouch directly through the capillaries in the blood stream.

It is indicated in this reference that a 5 gram lozenge when held in the mouth will release its active ingredient in a regular manner over a one and one half hour period. Larger lozenges will take longer periods to release the active ingredient.

Although the reference indicates that the composition, in the form of a lozenge, can be positioned in the buccal pouch and absorption of the active ingredient takes place through the mucous membrane, there is no disclosure that the lozenge becomes affixed to the mouth mucosa and maintains its position throughout the period that the drug is released.

A pharmaceutical preparation for oral cavity administration is also disclosed in U.S. Pat. No. 4,059,686, which issued on Nov. 22, 1977 to Tanaka, et al. The preparation is characterized as being a mixture of a pharmacologically active agent, a pharmaceutical carrier and sodium polyacrylate (PANA). It is indicated in the reference that when a proper quantity of the sodium polyacrylate is incorporated in the base carrier for a preparation for oral cavity administration, the sodium polyacrylate first absorbs water and adheres strongly to the local site, then swells and dissolves gradually at the site over a long period of time, while releasing the medicinal agent substantially uniformly. It is further indicated in the reference that it has been entirely unknown that sodium polyacrylate may be used as a base for a preparation for oral cavity administration and is effective in retarding disintegration.

In this reference, the sodium polyacrylate is merely blended with the carrier which can be microcrystalline cellulose, mannitol, anhydrous lactose or other commercially available products.

It is also indicated in this patent that the PANA used can be any of those used as food additives and its molecular weight, through not critical, is preferably about 185,000 to about 8,500,000 (the intrinsic viscosity is 0.4 to 1.1 [g/dl], as measured in 2N-NaOH at 30° C.). The amount to be added is 10 to 60% by weight based on total weight of the preparation.

The pharmacologically active agent suitable for administration according to the invention and intended to directly enter the systemic circulation include steroid hormones; proteins such as antiinflammatory enzymes and callicrein; peptides such as insulin, gastrins, secretin, pepstatin, and leupeptin; nitrate esters such as nitroglycerin and erythrityl tetranitrate; isoproterenol, and methacholine.

It is stated in the reference, that the pharmaceutical preparation is quite different from conventional buccal tablets and can stay in the oral cavity for 1 to 8 hours. As shown in FIG. 3 of the reference, release of Patent Blue employed in the test procedure was linear but the amount decreased with time.

It should also be noted that the sodium salt of acrylic acid is a water-soluble polymer which does not ensure a prolonged release of the drug. To achieve a minimum desired effect, the medication must contain a considerable proportion of polymer base, for which reason a small-size medication suitable for application to the mucous membrane of the mouth cavity cannot be developed. Ointments containing a sodium salt of acrylic acid as the base cannot ensure the desired accuracy of dosage, which is an essential condition for developing a medication containing a strong drug.

In U.S. Pat. No. 4,226,848, which issued Oct. 7, 1980 to Tsuneji Nagai, et al, a method and preparation for administering a medicament to the mucosa of the oral or nasal cavity is disclosed. In this reference, a water-swellable and mucose-adhesive polymeric matrix is employed which is comprised of 50 or more percent by weight of a cellulose ether and up to 50% by weight of a homo or copolymer of acrylic acid. It is indicated that the pharmaceutical preparation continuously releases the medicament at a controlled rate and causes the released medicament to be absorbed through the mucosa. It is indicated in the reference that a wide variety of medicaments can be employed in the preparation including an algesic and anti-inflammatory agents, antihistamines, topical anesthetics, vasodilators, oral antiseptics, drugs for the digestive organs, and a variety of other drugs including hypotensives, sedatives, antitumor agents and antacids.

When the cellulose ether and polyacrylic acid or its pharmaceutically acceptable salt are used singly in producing a pharmaceutical preparation, the resulting preparation is unsuitable as a slow-releasing preparation because it does not adhere to the mucosa of the oral or nasal cavity or even when it adheres, it is relatively rapidly disintegrated, dispersed or dissolved by the saliva or other secretions. In contrast, the pharmaceutical preparation of the reference containing a mixture of these in a specified ratio has sufficient adhesion to the mucosa, and does not dissolve, flow out and get out of shape although it is swollen and softened with the saliva or secretions. Moreover, the preparation, in accordance with the reference, does not irritate the mucosa of the oral or nasal cavity and releases the medicament uniformly over a long period of time either topically or through the entire body.

The specified ratio of the two polymers which form the polymeric matrix is indicated to be essential in order for the slow-releasing preparation of the reference not to cause whitening or blisters of the mucosa of the oral or nasal cavity, and also to release the medicament at a controlled rate.

When the amount of the acrylic acid polymer or its pharmaceutically acceptable salt is more than about 50% by weight, the pharmaceutical preparation irritates the mucosa of the oral or nasal cavity, and tends to cause marked whitening of the mucosa and the marked occurrence of blisters therein.

Preferably, the polymeric matrix used in the reference consists of about 65 to about 90% by weight of the cellulose ether and about 35 to about 10% by weight of the polyacrylic acid or its pharmaceutically acceptable salt.

The cellulose ether used in the reference is a cellulose derivative resulting from the partial or whole etherification of a plurality of hydroxyl groups of cellulose, and includes, for example, lower alkyl ethers, hydroxy lower alkyl ethers, and carboxy lower alkyl ethers of cellulose. It is also stated in this patent that the rate of releasing the medicament can be controlled easily to suit the purpose of therapy by changing the ratio between the cellulose ether and the acrylic homo- or copolymer or its pharmacetically acceptable salt, within the specified range.

Additionally, at column 7, lines 55 et seq. of the reference, it is indicated that the preparation of the invention swells upon absorption of saliva and gradually releases the medicament at a controlled rate. There is no indication that the medicament is absorbed immediately and at a uniform rate.

Although the preparation is capable of swelling and adhering to the mucous surfaces of the mouth and nose, it does not dissolve in saliva or secretions (column 8, lines 9–17). At the end of its action, the medication is removed from the mouth or nose cavity. The method and compositions are characterized by disadvantages in that the preparation is insoluble, the duration of the effect of the medication is difficult to determine, and the preparation is inconvenient to use because it requires removal by the patient. Moreover, the medications according to this Pat. No. 4,226,848, are dispersions, for which reason they are relatively nonuniform and may affect uniform drug release.

A sustained release therapeutic composition is disclosed in U.S. Pat. No. 4,226,849, filed June 14, 1979, subsequent to the effective filing date of the present invention, which issued to J. M. Schor and is also assigned to Forest Laboratories, Inc. of New York. In this patent, it was reported that a significantly greater control of the release pattern is achieved by a chemical modification which results in an increase in carboxyl functionality in the hydroxypropylmethylcellulose molecule. Although the actual mechanism is not known, it was speculated that the slower release rate arises from a decreased rate of swelling or a lower water solubility resulting from a hydrogen-bonding interaction between the carboxyl and the carbonyl and/or hydroxyl groups in the hydroxypropylmethylcellulose which has been subjected to both hydrolysis and oxidation.

In contrast to the disclosure of U.S. Pat. No. 3,870,790, the earlier Forest Laboratories, Inc. patent, it is indicated by the patentee that moisture contents as low as 0.5% can be present during the preparation of tablets and other compressed solid shapes. The amount of moisture present influences the amount of pressure necessary to prepare the shaped objects and the integrity thereof, but plays a minor role as compared to the chemical structure in the rate or release of medicaments from the chemically modified hydroxypropylmethylcellulose. Similarly, while the release pattern is governed at least in part by the size of the tablet or other shaped object as well as by the degree of compression, the chemical structure of the hydroxypropylmethylcellulose which has been subjected to chemical modification superimposes its effect and is the dominant factor in the control of the release rate.

Drugs embedded in the "Synchron" Carrier System, as the patentee terms the carrier base, are intended to attain and maintain a steady concentration of drug in blood or tissues. One objective in using these preparations is to reduce the dosage frequency, to make therapy simple and convenient, and to improve compliance by the patient. In addition, by maintaining a reasonably constant plasma concentration of drug, excessive or premature peaking is avoided and side effects, which may be associated with peak concentrations of drug, would be lessened. In addition, a more uniform concentration of drug in blood and tissues is much more likely to be paralleled by a more uniform pharmacologic effect and response. With dissolution being the main rate-limiting step in drug absorption, the rate of solution of the drug from the dosage form into the surrounding fluids at the absorption site is controlled by the chemical changes induced during production of the "Synchron" Carrier System. The drug can further be released to a specific site at a uniform rate independently of the pH environment, resulting in steady concentrations of the drug in tissues. Drugs incorporated into the "Synchron" Carrier System vehicle are prone to be absorbed completely, but more slowly, and are formulated to maintain the therapeutic effective level of the particular drug and to produce a prolonged response and a diminished rate of unassimilated drug elimination.

In an article by Ishida et al., Chemical and Pharmaceutical Bulletin, 29(3) 810-816, March 1981, entitled "New Mucosal Dosage Form of Insulin" attempts to prepare a new oral mucosal dosage form of insulin with a view to solving problems encountered by injections were reviewed. The oral mucosal dosage form of insulin consisted of the core-base which contains cacao butter, insulin and an additive, and the peripheral-base which contained a mixture of hydroxypropyl cellulose-H (HPC) and Carbopol-934 (CP). The suitable mixing ration of HPC and CP in the peripheral-base was chosen as 1:2 on the basis of experimental results concerning the stickiness, dissolution properties, viscosity and fracture resistance. This dosage form could stick tightly to the oral mucosa of beagle dogs for 6 hours.

In a preliminary experiment, a compressed disc which consisted of HPC, CP and insulin was applied to the oral mucosa in beagle dogs. No absorption of insulin was found possibly for the following two reasons: (1) Only a very small amount of insulin reached the membrane because insulin was released in all directions and the part released into saliva was swallowed and inactivated, (2) HPC and CP seemed to be unsuitable as the base materials for mucosal absorption of insulin.

In order to find a suitable mixing ratio of HPC and CP for use as the peripheral base, the stickiness to the mucosal membrane, dissolution properties, viscosity of the solution and fracture resistance, were investigated. No clear relationship was found between the mixing ratio of HPC and CP and the stickiness to the mucosal membrane, suggesting that the stickiness was related to the content of moisture on the membrane. The tablet did not stick to a very moist membrane but stuck tightly to one with little moisture. If the moisture level was satisfactory, however, a tablet containing more CP usually stuck more tightly to the mucosal membrane for a longer time period. Thus, in order to affix this tablet to the oral mucosa, it is necessary to wipe away the saliva with absorbent cotton.

Product information reports were available in September, 1981 and January, 1982 from Merrell Dow Pharmaceuticals, Inc. on transmucosal tablets marketed under the name "Susadrin". Reference is made in these reports to the "Synchron System" mentioned in the above cited Lowey and Schor patents both of which are assigned to Forest Laboratories, Inc. The first report dated September 1981, "Susadrin TM (nitroglycerin), transmucal tablets—Product Information and Clinical Summary—Merrell Dow" was 8 pages in length and indicated that Susadrin tablets have demonstrated activity at, the earliest period measured, 3 minutes after placement in the buccal pouch and a duration of activity of up to 6 hours.

Another Merrell Dow report entitled "How to Benefit most from Susadrin TM (nitroglycerin) Transmucosal Tablets", an 8 page brochure, provides directions to a patient for whom Susadrin tablets have been prescribed. The report states that:

"Susadrin Transmucosal Tablets are a unique clinically proven way to deliver nitroglycerin to your system. Rather than placing it under your tongue (like a sublingual tablet) or swallowing it, you place Susadrin between the upper lip and gum or in the buccal pouch. Within minutes, it will adhere comfortably and begin releasing medication. It will continue to release medication until it dissolves. In some cases, the tablet isn't completely gone even after five hours."

"After the Susadrin Tablet is in place for a minute or two, it will adhere comfortably to the oral mucosa. From then on, the tablet is not easily dislodged, and you may talk, eat, and drink quite normally while the tablet is in place. You will also find that a properly placed tablet is not noticeable to others.

The average dissolution time for a Susadrin Transumcosal Tablet is three to five hours, but the rate at which Susadrin Transmucosal Tablets dissolve in your mouth can depend upon you. For example, touching the tablet with your tongue or drinking hot liquids, tends to increase the rate at which the tablet dissolves."

A third report by Merrell Dow is entitled "Transmucosal Nitroglycerin (Susadrin TM) in the treatment of Angina Pectoris". Report number 1 is a 7 page discussion of Susadrin and indicates that Susadrin tablets represent a new nitrate delivery system that provides rapid onset, activity at three minutes—and prolonged duration of action—up to 5 hours of angina prophylaxis.

The report is mainly concerned with the results obtained by five leading investigations and indicates that to the date of the report, the results of 50 patients have been received.

In an article by S. S. Davis, et al entitled "Cintigraphic Studies in the In Vivo Dissolution of a Buccal Tablet", which was published in Modern Concepts in Nitrate Delivery Systems, Royal Society of Medicine, International Congress and Symposium Series No. 54, Pgs. 30–37, 1983, it was disclosed that the therapeutic efficacy of drugs with short biological half lives can be improved by the use of sustained-release formulations that provide a slow and controlled input of drug to the systemic circulation. In the experimental work reported in this reference, sustained-release dosage forms of glyceryl trinitrate were employed in tablets, ointments and adhesive patches. Buccal tablets were evaluated wherein the drug was entrapped in a slow eroding non-disintegrating tablet base or matrix such a s hydroxypropylmethyl cellulose.

The buccal tablet employed resembled a conventional tablet, but in this type of formulation, the drug was entrapped in a slowly eroding non-disintegrating tablet base or matrix. Modified hydroxypropylmethylcellulose of the type disclosed in the Forest Laboratories, Inc. U.S. Pat. No. 4,226,849 discussed above, was indicated to be a suitable matrix material. On contact with water, the hydroxypropylmethylcellulose forms a gel-like layer and it is thought that the release of the drug contained in the matrix is controlled by diffusion of the drug through the gel layer and erosion of the gel itself.

Although hydroxypropylmethylcellulose used in the above-described medications prolongs the effect of nitroglycerin, the prolongation is insufficient because of its high hydrophilicity. For this reason, hydroxypropylmethylcellulose cannot be used as a basis for manufacturing a medicinal film similar to ocular medicinal films. Moreover, a sufficient prolonged effect is only achieved at a high proportion of the methylcellulose. In this connection, buccal tablets having a considerable weight (132 mg) are normally employed. Application of these tablets to the mucosa of the mouth cavity is therefore inconvenient for the patient. Additionally, hydroxypropylmethylcellulose has a low adhesive capacity relative to the mouth mucosa.

The reference further states that the in vitro release characteristics of a matrix system can be measured using a standardized dissolution test. However, the behavior in vivo is more difficult to assess; a possible approach would be the repeated administration of buccal tablets to the same volunteers and assaying individual tablets after different contact times. This approach would be extremely tedious to undertake and a more satisfactory alternative was proposed which involved the use of external scintigraphy to monitor the release of a gamma emitting radionuclide. However, practical considerations prevented the labelling of the drug directly and, therefore, a technetium-99m-labelled diethylenetriamine pentaacetic acid was used as a model.

It was stated in this reference to Davis et al. that four volunteers placed the tablets on separate occasions in the upper buccal cavity, the lower buccal cavity, or behind the lower front incisors. The release rate from the tablets placed behind the lower front incisors was much faster than for the tablets placed in the buccal cavities. For two of the four volunteers, there was no difference in release rate for upper and lower cavities but for the others, the release rates were very different (Table A).

TABLE A

The effect of position on the release of $^{99m}$Tc-DTPA from a sustained-release buccal tablet

| | Percentage released in 2 h | | |
|---|---|---|---|
| Subject | Lower front incisors | Lower buccal | Upper buccal |
| AH | 71 | 17 | 19 |
| RK | 96 | 18 | 15 |
| MS | 95 | 22 | 70 |
| PP | 94 | 13 | 65 |

To determine the effect of chewing and drinking, two subjects placed the sustained release tablet in the lower buccal cavity and then at predetermined times, performed a set pattern of chewing and drinking. The release pattern of the $^{99m}$Tc-DTPA was not changed to any marked extent.

It was concluded in this article that the buccal sustained release system based upon a hydroxypropylmethylcellulose matrix (Synchron) provided a slow release of entrapped materials. It was therefore a suitable material for the administration of glyceryl trinitrate.

The release patterns from tablets placed in the lower buccal cavity show greater inter-subject variation than was observed within individuals. The position of the tablet (upper or lower buccal cavity) could be important in some individuals. However, a consistent pattern of release should be obtained in the same individual, so that a given patient could be titrated to a given regimen. Eating and drinking appear to have little effect on release rates.

In another article by S. S. Davis et al. entitled "Design and Evaluation of Sustained Release Formulation for Oral and Buccal Administration" Adv. Pharmacother. Vol 1, pp 17–25 (Karger, Basel 1982), the Synchron controlled release system was discussed. In this article, radio—labelled tablets were employed and the subjects receiving the tablets were seated against the face of a gamma camera. Each subject received a rapidly dissolving tablet which was placed in the lower buccal cavity, followed on a second occasion by the sustained release buccal tablet—the rapidly dissolving tablet had dissolved completely after 20 minutes while the sustained release Synchron formulations was still releasing the marker after 3 hours. This article concluded with a discussion wherein Dr. Davis was asked whether he ever experienced a patient that could dissolve the buccal tablets within 10 minutes. In reply Dr. Davis stated:

"We found, with volunteers who had dry mouths, that we got a very slow release. But in no occasion did we find a very rapid release with these formulations. 10 minutes sounds very quick for the Synchron system. A much slower release than that would be expected. I have a feeling that the volunteer or patient was doing something unusual with the tablet. For example, moving it around the mouth, rather than letting it remain stationary in the buccal cavity."

In a further study involving the evaluation of the Synchron system; P. B. Daly et al. authored an article entitled "Scintigraphic assessment of the in vivo dissolution rate of a sustained release tablet", International Journal of Pharmaceutics, 10 (1982) 17–24. It is stated that with respect to slow release systems, the basic process of release from a matrix is leaching of the medicament by the surrounding fluid which is able to permeate into the matrix through pores and interparticulate spaces. The drug dissolves into this fluid phase and diffuses from the system via capillary channels. In the case of 'Synchron', the surface of the tablet swells to a gel-like consistency following drug release by a combination of diffusion and surface erosion.

Additionally, the "Synchron" system does not provide satisfactory results because of its physico-chemical properties, since when it is used, the prolongation effect is achieved due to the presence of a large amount of hydroxypropylmethylcellulose. Thus, the weight of the Susadrin buccal tablets is quite large (132 mg). The application of such tablets to the mouth mucosa is not convenient for the patients. Such tablets do not have high adhesion to the mouth mucosa. In contrast, applicants antianginal film is in the form of thin plates with high adhesive qualities for the mouth mucosa. As hereinafter indicated in the examples, a comparative study of the effect of nitroglycerin, Trinitrolong® (applicants' films) and Susadrin is set forth. It has been demonstrated that the arresting effect of Susadrin tablets, given to 8 patients with typical angina pectoris of effort, which was successfully reproduced under the load on a treadmill, was registered in only one patient, as long as nitroglycerin tablets were sublingually provided for arresting effect in 6, and Trinitrolong—in 5 patients, suffering angina pectoris (the tablets were given to the patients under the conditions of continued physical load after the beginning of the attack). Consequently, the arresting effect of applicants' antianginal plate was equal to the effect of ordinary nitroglycerin tablets taken sublingually, and the arresting effect of Susadrin was noted in only one of the eight patients.

In an article published in the USSR entitled "Trinitrolong®—A New Nitroglycerin Drug with Prolonged Effect" by V. I. Metelitsa, et al, Terapevticheskiy Arkhiv. 52/5, 54–59 (1980), clinico-pharmacological studies of Trinitrolong®, also referred to as TNL, were made of forty-three patients with ischemic heart disease. As reported in the reference, acute pharmacodynamic studies, as well as the study of efficacy, were conducted in comparison with the effect of well known nitroglycerin drugs. The results of comparison of the pharmacodynamic effect of Trinitrolong used in the form of a plate for application of the gums and nitroglycerin in the form of tablets for sub-lingual use were presented. When using Trinitrolong, the hemodynamic effects were observed in the first one-two minutes after application of the plate, and lasted on the average for three to four hours. According to the data, repeated individual selected standard physical loads with the treadmill in combination with EKG monitoring, the ST segment had a stable uniform depression before drug administration. The effect of the drug, according to the changes of the value of ST segment depression after drug administration, was shown to differ from the dynamics of the effect of a placebo that is, the natural dynamics of the shift of the ST segment in the patients with ischemic heart disease during loads.

The long term use of Trinitrolong in nine patients with ischemic heart disease confirmed the effectiveness of the drug in relation both to the decreased average frequency of attacks of angina pectoris and the number of tablets of nitroglycerin used during the attacks, as well as the average volume of work done during testing on a bicycle ergometer. The best effect was noted when using the Trinitrolong in the form of plates affixed to the gums. It was concluded in the above mentioned Metelitsa et al. publication that the use of Trinitrolong in the form of a plate on the mucous membrane makes it possible to quickly arrest attacks of angina pectoris and at the same time, to uniformly prolong the effect of nitroglycerin for three to four hours and more. It was also indicated that the method of individual dosage of Trinitrolong made it possible to improve the efficacy of treatment when taking minimum doses or less of nitroglycerin and at the same time, to avoid side effects which sometimes occur after taking nitroglycerin. In another article by S. Yu. Martsevich and V. I. Metelitsa entitled "Comparison of the Effect of Trinitrolong Plates and Nitroglycerin Tablets in Arresting Attacks of Stress Angina Pectoris", Terapevticheskiy Arkhiv. 53(4); 16–18(1981), there is described a study of nine ischemic heart disease patients with typical stress angina pectoris. These patients frequently had pain of considerable intensity and fast acting medicinal agents were required.

Nitroglycerine tablets taken sublingually have been successfully used to this end for 100 years. However, the duration of action of the latter is not over 20–30 min. Therefore, it does not always protect patients from repeated angina pectoris attacks. Prolonged action nitroglycerine preparations recently developed (Sustac, Nitrong, and the like) do not provide a rapid effect. Therefore, they cannot be used to arrest angina pectoris attacks. The new long acting preparation Trinitrolong® (TNL) combines the properties of nitroglycerine for sublingual use and prolonged nitrates, and it is intended for both long term prophylaxis of angina pectoris attacks and for their rapid arrest.

In this comparison, all patients underwent continuously increasing graduated work loads on the bicycle ergometer by the standard protocol.

On the test day, the patients underwent 3 bicycle ergometer work periods at least 4 hour intervals. The patients developed a typical angina pectoris attack during each work period. The first work period was the control. When the second work period ended, the patients were given 0.5 mg nitroglycerine sublingually. Upon stopping the third, a TNL plate, which contained 2 mg nitroglycerine, was applied to the front of the upper gums above the teeth or in small incisions. The duration of the angina pectoris attacks was recorded by stopwatch. The EKG (leads $V_3$–$V_6$) and arterial pressure were recorded at the end of each minute of working and rest.

It was indicated that the preparations were effective to the same degree in arresting a stress angina pectoris attack. Both the sublingual use of the tablet and application of TNL to the mucosa of the upper gum equally rapidly removed pain and eliminated indications of myocardial ischemia on the EKG.

While arresting an angina pectoris attack, TNL retains its prophylactic effect for 3–4 hours and longer. A combination of the capacity of TNL to rapidly reduce an angina pectoris attack and have a prolonged prophylactic antianginal effect makes the preparation particularly valuable in the treatment of patients with frequent angina pectoris attacks of effort and at rest.

A further article by Savvateev et al. "THE PHAPMACODYNAMICS OF TRINITROLONG AND SUSTAC ACCORDING TO THE DATA OF TESTING WITH PHYSICAL LOAD", Terapevticheskiy Arkhiv, 53(1); 49–53(1981) discloses a study of the special features of pharmacodynamics of preparations of nitroglycerin with prolonged effect, in particular the new drug Trinitrolong (TNL) in the form of a plate containing 2 mg of nitroglycerin for application to the mucous membranes of the mouth and in the form of capsules for internal administration. The effect of Sustac containing 6.4 mg of nitroglycerin was also studied.

The study was made on 21 males suffering from IHD; their ages ranged from 38 to 63 (the average age was $51\pm6$ years). The duration of the illness varied from ½ a year to 12 years (on the average 2.7 years). All of the patients suffered a typical stable angina pectoris of effort with frequency of attacks from 1 to 12 in 24 hours. In 9 patients, there have been myocardium infarcts in the past documented by the presence of a pathological wave Q on the EKG at rest. Coronaroangiography was conducted on 7 of the patients (L. S. Matveyeva and V. P. Mazayev) which confirmed the presence of an atherosclerotic stenosing process with a decrease in the main branches of the coronary arteries for more than 75% of their lumen. In 8 of the patients, the EKG at rest was characterized by symptoms of scar damage to the myocardium; the other 13 patients were normal. At the same time, in all of the patients during bicycle ergometry test on the EKG, one could observe undoubted symptoms of myocardium ischemia in the form of horizontal or downsloping depression of the ST segment by 1.5 mm and more which, in all cases, was accompanied by angina pectoris stress. The threshold value of the double product (DP) after application of TNL amounted to $235.9\pm15.9$ and for the control test—$175.0\pm8.6$ (p 0.001). Then the decrease of the depression of the ST segment after application of TNL amounted to $1.60\pm0.15$ mm that is during the control test was less than—$1.90\pm0.16$ mm (p 0.05). Four patients who had a background of taking TNL showed a marked increase in tolerance to work; it was necessary to stop the test due to general fatigue without having achieved the criteria for stopping the test that is without ST segment depression and/or angina pectoris attack. Other drugs did not show such a marked increase in tolerance and difference in the decrease of the depression of the ST segment; in comparison with the control test they proved it to be not so perceptible. Moreover, the DP (DP is maximal heart rate x systolic blood pressure) for each patient was calculated after giving Sustac and TNL for application on the gums at a fixed point in the load that is, at an intermediate point corresponding to the maximum volume of work completed on the bicycle ergometry in the control tests. At this same work level, the value of the DP after taking the nitroglycerin drugs was smaller than the control. The difference was significant for TNL (p 0.05). At this same fixed point of the work load, the degree of decrease of the depression of ST segment was proven to be smaller (p 0.01) for all nitroglycerin drugs in comparison with the control. In this article, it was concluded that Trinitrolong, a new nitroglycerin drug with a prolonged effect in the form of a plate for application on the mucous membranes of the upper gum, and to a lesser degree, Sustac and medicinal film in capsules per os, cause an increase in tolerance to work load with a bicycle ergometry test in patients with ischemic heart disease verified in comparison with a placebo.

A 15 page brochure by Davidov, Khromov, Metelitsa, Sarycheva and Babajan entitled "Trinitrolong", published by the Ministry of Public Health of the U.S.S.R. also presented a review and evaluation of the use of Trinitrolong for the treatment of cardiovascular diseases. It is indicated in this article that due to its hydrophilic nature, the thin oval plates containing the Trinitrolong stick easily to the mucous membrane and gradually release nitroglycerin. Immediately after the application of the plate, their required therapeutic effect is observed that lasts from two to four hours or more. The steady nitroglycerin release, as well as the optimal dosage adopted to the individual requirements of the patient, decreases side effects considerably. In patients administered 0.5 mg. pills of sublingual nitroglycerin, peripheral hemodynamic effects were observed within one minute, and the optimum effect was reached within five minutes. However, after thirty minutes, the effect of the pill had disappeared. In application of a two milligram Trinitrolong plate to the gum of the same patients, peripheral and central hemodynamic effects were observed within one minute, and the optimum effect was reached within thirty minutes and lasted on the average for three hours, depending on the individual ability to dissolve the polymeric membrane. During physical exercise and after application of Trinitrolong to the mucous membrane of the oral cavity, patients demonstrated a decrease in the ST-segment depression to its complete normalization.

In U.S.S.R. Inventors' Certificate No. 810,241, assigned to the same assignee as the present invention and published March 7, 1981 by the same inventors of this application, a method is claimed for individual dosaging of film forms of medicinal agents employing an absorbable polymeric carrier film which can be attached to the buccal mucous membrane. Illustrative of the film, which is a resorptive polymeric carrier film, are polymers and copolymers of polyacrylic acids. It is indicated in the Inventors' Certificate that according to the invention, it is possible to maintain a continuous pharmacodynamic effect which is more uniform than that obtained by previously known methods.

A film-carrier was secured onto the mouth mucous membrane without a medicated compound in order to determine its resorption time and, hence, possible time of penetration of the medicated compound into the body. Then a film was selected with a content of the medicated compound which would be sufficient to penetrate into the body during the established period of the film resorption. Thereafter the film with the medicated compound was bonded one or more times on various areas of the mouth mucous membrane. The glued film became resorbed whereby the medicated compound was permanently resorbed directly by the mouth mucous membrane. In this manner it passed into the systemic blood circulation avoiding the liver. This ensures prevention of the medicated compound from decomposition by liver enzymes or contents of the gastroenteric tract. During the entire period up to a complete dissolution of the film (several hours) the therapeutic concentration of the medicated compound in the blood was retained and the required permanent pharmacodynamic effect ensured.

In the first example of the Inventor's Certificate a film-carrier without a medicated compound weighing 13 mg was bonded to the mouth mucous membrane of a volunteer in the region of the upper gingiva over the premolar tooth. After 1.5 hours the film was fully resorbed. On the basis of the available data on pharmacokinetics of nitroglycerin, to maintain a constant therapeutical concentration of the preparation in the blood, it was indicated that 0.5 mg of nitroglycerin should be administered every half an hour. Consequently, 1.5 mg of nitroglycerin should be administered to the given patient over 1.5 hours. The film corresponding to the established dose i.e. 1.5 mg, is selected from a series of polymeric films with different contents of nitroglycerin. The selected film with a mass of 15 mg consisting of a base (a copolymer of acrylamide, vinylpyrrolidone and ethylacrylate) and nitroglycerin contained in an amount of 10 to 30% by mass of the film or plate was fixed to the mucous membrane of the top jaw gingiva. The time of occurrence, duration and level of the effect were evaluated by the method of tetrapolar impedance plethysmography from a limb through the variation of the amplitude of waves "a" and "b" before and after administration, of a film with nitroglycerin with the data before and after sublingual administration of a granule of nitroglycerin. Analysis of the curves showed that the method according to the Inventor's Certificate made it possible to obtain a pharmacodynamic effect within several minutes in both instances. However, in the sublingual method this effect gradually diminished and stopped after 20-30 minutes, whereas the method disclosed in the Inventor's Certificate made it possible to maintain a continuous pharmacodynamic effect for 1.5 hours and longer, i.e. several times longer and more uniform than by sublingual administration. In a second example, the film-carrier without the medicated compound as described was applied to the mucous membrane of the jaw gingiva of a patient. The film was fully resorbed after 110 minutes. Thereafter, on the basis of the pharmacokinetics of nitroglycerin, the patient should be administered the medicated compound in a dose of 2 mg over 2 hours to maintain a permanent therapeutic concentration of the preparation. The film corresponding to the established dose, i.e. 2 mg, was selected from a series of polymeric films with different contents of nitroglycerine. The selected film weighing 15 mg and consisting of a base (copolymer) and nitroglycerin in the dose of 2 mg was fixed to the mucous membrane of the upper jaw gingiva. The evaluation of the pharmacodynamic effect was performed by the method of tetrapolar impedance plethysmography of a finger of the patient before and after the administration, of the film with nitroglycerin in comparison with the data before and after the sublingual administration of a granule of nitroglycerin (0.5 mg). Analysis of the data shows that the method of application of the medicated compound with the individually selected dosage made it possible to obtain the pharmacodynamic effect within 2 minutes and this effect lasted uniformly for 110 minutes. The return to the initial state was recorded by the end of the second hour from the moment of administration of the preparation.

In a third example in the Inventor's Certificate, a film-carrier without the medicated compound weighing 25 mg was fixed onto the mouth mucous membrane in the area of upper gingiva of a patient. The polymeric film was bonded after 30 seconds due to its swelling upon contact with saliva. The film was fully resorbed within 4 hours 45 minutes. Therefore, on the basis of the data on pharmacokinetics of nitroglycerin, 4.5–5 mg of nitroglycerin should be administered to this patient within 4.5-5 hours. A film with the content of 5 mg of nitroglycerin was selected and fixed to the mucous membrane of the mouth cavity in the region of the upper gingiva. Analysis of the obtained data showed that in the patient the polymeric film was resorbed over a period 3 times longer than in the first example and to ensure the permanent pharmacodynamic effect during this time the film should be used with the polymeric carrier containing the triple dose of nitroglycerin. However, such a dose would have caused undesirable side effects in the patient of the first example.

Finally, a film-carrier without preparation according to the first example and weighing 25 mg was fixed to the upper gingiva mucous membrane of a patient. The film was bonded to the mucous membrane within 1–2 seconds. The film was fully resorbed after 38 minutes. Therefore, during this period the patient should not be given more than 0.5-1 mg of nitroglycerin. The film with 1 mg of nitroglycerin was selected and bonded to the mouth mucous membrane. Analysis of the data showed that the polymer film in the patient was resorbed about 8 times more rapidly than in the patient of the third example. Consequently, the administration of a dose 8 times lower than that of the third example made it possible to maintain the therapeutic effect within the established period of time without any undesirable side effects.

In U.S.S.R. Inventors' Certificate No. 806,037, also assigned to the same assignee as the present invention and published Feb. 23, 1981 by the same inventors of this application, there is disclosed an antianginal preparation, which has prolonged action and reduced side effects. The antianginal preparation contains a water soluble carrier homopolymer of acrylamide, n-vinylpyrrolidone or their copolymers with acrylates. It is indicated in the Inventors' Certificate that the preparation can also contain dispersions of solid fats with melting points of 30° to 50° C. in order to insure a prolonged effect.

In USSR Inventor's Certificate No. 387,559, also assigned to same assignees and which corresponds to U.S. Pat. No. 3,935,303, there is disclosed polymer-base ocular medicinal films which are relevant to the antianginal film of the present invention. The ocular medicinal films are not suitable, however, in that they are only based on water-soluble polymers which, according to the inventors, dissolve completely in lachrymal fluids within 30 to 40 minutes. Unlike the conjunctival cavity, where polymer solutions are retained for a considerable time, polymer solutions resulting from dissolution of such films in the mouth cavity disappear relatively rapidly. Therefore, films dissolving within a relatively short time do not ensure the required prolonged effect, i.e., a few hours, when used as nitrate-containing medications applied to the mucosa of the mouth cavity.

The main object of this invention is to provide a novel medicinal form, viz., a medicinal plate having antianginal action, characterized by prolonged action, improved accuracy of dosage of the active substance which is soluble in saliva and stable in storage.

The specific object of the invention is to provide a novel medicinal form, namely, an antianginal plate which can be used as a medicinal preparation characterized by prolonged action, increased accuracy of dosage of the active principle, and stability in storage.

SUMMARY OF THE INVENTION

These objects have been attained with an antianginal film, according to the invention, which is a 0.1 to 1.5 mm thick plate consisting of a biologically soluble and resolvable carrier, such as a homopolymer of acrylamide or vinylpyrrolidone, or a copolymer thereof with an acrylate, containing from 99 to 70 per cent by weight of acrylamide with vinylpyrrolidone, from 1 to 30 per cent by weight of an acrylate having a molecular mass of from 50,000 to 1,000,000, and an active substance exhibiting an antianginal activity, said components being present in the following proportions, in per cent by weight:

| | |
|---|---|
| Active substance having antianginal action | 3.0–30.0 |
| biologically soluble and resolvable carrier | 70.0–97.0 |

In order to prolong its action, the medicinal plate also contains dispersed solid fat melting from 30° to 50° C., taken in the quantity of from 3 to 30 per cent by weight with respect to the weight of all other components.

It is recommended that the antianginal plate contain cocoa butter, hydrogenized cotton-seed oil, glycerol laurate or phthalate, as the dispersed solid fat.

The proposed film preferably contains a copolymer of acrylamide vinylpyrrolidone, and ethyl acrylate, taken in the ratio of 0.6:0.2:0.2 respectively, or a copolymer of acrylamide, vinylpyrrolidone, and butyl acrylate, taken in the ratio of 1.0:0.5:0.3 respectively, or a copolymer of equal quantities of acrylamide, vinylpyrrolidone and ethyl acrylate, as a biologically soluble and resolvable carrier polymer.

The proposed antianginal plate preferably contains glycerol trinitrate, isosorbide dinitrate, or pentaerythritol tetranitrate as the active principle.

The selection of the biologically soluble and resolvable carrier from homopolymers of acrylamide and vinylpyrrolidone and their copolymers with acrylates taken in the specificed ratios, depends, according to the invention, on the ability of said polymers to dissolve in the liquid media of the body, their harmlessness, and ability to form labile complex bonds with the active principle of the preparation. Solid fats incorporated in the proposed medicinal film, regulate its hydrophobic properties to control the rate of liberation of the active principle from the swollen antianginal plate.

The proposed antianginal plate can be taken in capsules or be applied to the mouth mucosa. The latter method of administration is a novel method and has not been described in the literature. It makes it possible to treat ischemic heart disease by individual doses.

According to the invention, the method of treating ischemic heart disease with the proposed antianginal plate by individual doses, consists in that a plate of a biologically soluble and resolvable carrier polymer containing no active principle of antianginal action, is first applied to a chosen site of the mouth mucosa of the patient, and the time of resolution of the plate is determined. This time characterizes the possible time during which the active substance will pass to the body. Next a plate is selected containing that amount of the active principle which should be given to the patient during the time of resolution. Finally, said plate containing the required amount of the antianginal preparation is applied (once or repeatedly) to the chosen site of the mouth mucosa of the patient to ensure continuous and optimal therapeutic efect during the entire period of dissolution of said plate.

The main advantage of the proposed method of treating ischemic heat disease is that the active principle is delivered directly into the systemic blood flow bypassing the liver, the preparation intake being uniform in the course of a prolonged period of time.

DETAILED DESCRIPTION OF THE INVENTION

Figure 1:
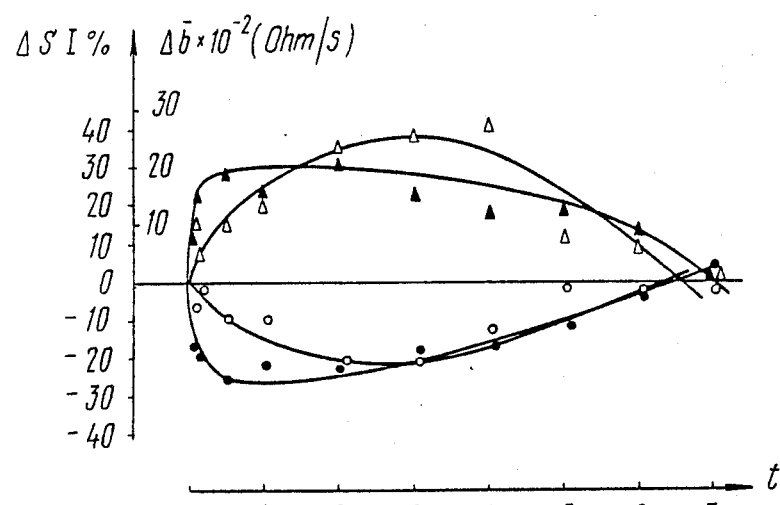

Antianginal plates were tried in a clinic. The clinical trials had the following objects: (1) to carry out comparative studies of pharacodynamics of the antianginal plate containing glycerol trinitrate and the known preparation Sustac as the active substance, both preparations being given per os; (2) to study the pharmacodynamics of the proposed antianginal plate, containing glycerol trinitrate, by applying it to the mouth mucosa, and tablets of glycerol trinitrate given sublingually.

The pharmacodynamic effects were assessed by the central and peripheral, hemodynamic indices, and also by the changes in tolerance to physical exercise. Earlier we had established the correlation ($r=0.81\pm0.06$; p 0.001) between the dynamics (under the effect of nitrates) of the peripheral and central blood circulation indices and the results of the ECG-monitoring with controlled physical load. This helped us judge the efficacy of the proposed antianginal plate containing glycerol trinitrate by studying analogous hemodynamic parameters.

The proposed medicinal plate containing glycerol trinitrate was administered to 23 male patients aging from 37 to 62 (average age, 48) with ischemic heart disease manifested in angina pectoris, with 1 to 15 attacks a day; seven patients had myocardial infarction in the past (with ECG records). The clinical manifestations of the disease averaged from five months to 12 years. 21 patients were tested by bicycle ergometry: 12 of them showed low tolerance for physical work, medium tolerance was in 5 and high in 4 patients. The mean load in the test group was 421.4 kg-min; the work done was 2260 kg-m. Thirteen patients had three main branches of the coronary arteries affected; two branches were affected in one patient, and one branch in four patients; no local stenoses of the coronary vessels were found in the remaining three patients. Three patients had initial signs of cardiac insufficiency. Patients with marked arterial hypertension were not studied.

The following study methods were used: finger impedance plethysmography (FIP), impedance cardiography, ECG-monitoring with controlled physical work load, and bicycle ergometry.

FIP was used to assess the peripheral vascular action of the medicinal film containing glycerol trinitrate by the size of the first negative wave "b" on the first derivative of plethysmogram curve (b). This value was expressed in $10^{-2}$ Ohm/sec.

Impedance cardiography was used to determine the stroke volume of the heart, from which the stroke index (ml/sq.m) was determined.

ECG-monitoring with controlled physical work load was used to study the dynamics of the depression of the ST segment under repeated individual selected standard physical work loads during many-hour ECG-monitoring with a portable monitor with subsequent computer analysis of the electrocardiogram. At one-hour intervals, the patient was given by the doctor the same individual selected repeated standard physical work load with treadmill and the action of the proposed antianginal plate containing glycerol trinitrate was assessed by the decrease in the depression of the ST segment (as compared with the initial one).

The index of ST(D) segment standard depression, characterizing the change in the depression per pulse increment unit was used to assess the efficacy of the proposed antianginal plate.

During the bicycle ergometry, the continuous work load was increased in steps, beginning with 150 kg-m/min for three minutes, with subsequent 100 per cent increase in the work load. ECG was taken with 12 standard leads; the arterial pressure and the respiration rate were measured at the second minute of each work load step. The work continued (in the absence of contraindications) until horizontal or downsloping depression of the segment ST to at least 1 mm was attained or until an attack of angina pectoris developed. The following indices were analyzed; intensity of the work load and the volume of the work done; pulse rate and arterial pressure at the initial and at the peak load; time of continuous work on the bicycle ergometry until signs of myocardial ischemia developed.

Drug therapy was suspended 24 hours before the tests (except glycerol trinitrate for sublingual administration to arrest angina pectoris attacks). The initial control indices of FIP, the impedance cardiographic indices and arterial pressure were recorded in 2–3 hours after a light breakfast. During ECG-monitoring tests, each patient was given a specifically selected starting physical work load.

On the first day of the studies, all patients were tested for sensitivity to nitrates by sublingual doses of 0.5 mg of glycerol trinitrate in tablets. Patients who showed normal sensitivity to nitrates were later given Sustac, (6.4 mg of glycerol trinitrate) or capsules of glycerol trinitrate (6.0 mg), while patients with low sensitivity to nitrates were given Sustac (12.8 mg) or glycerol trinitrate capsules (9.0 mg).

The dose of the proposed antianginal plate containing glycerol trinitrate for application to the mouth mucosa was determined depending on the time of resolution of the carrier without the active principle (glycerol trinitrate). To determine individual doses of the antianginal plate containing glycerol trinitrate, the doctor applied the polymer carrier (without the active principle) to the mouth mucosa, namely in the region of the upper gum above the canines or premolars, and determined the time during which the film fully resolved. Next he chose the anti-anginal plate containing the required amount of glycerol trinitrate which would ensure continuous and optimal therapeutic effect during the time of full resolution of the plate.

Approximate calculation: 0.3–0.5 mg of glycerol trinitrate per each 30 minutes of plate resolution. The selected type of the antianginal plate containing the corresponding dose of glycerol trinitrate, namely 1 mg for 60–90 minuts of resolution), or 2 mg (for 2–3 hour resolution), or 3 mg (to 6 hours of plate resolution) can then be practiced by the patient himself, who applied the plate to the gum mucosa on the same or the opposite side.

Each pharmacodynamic study was continued from 6 to 7 hours. The hemodynamic indices were recorded at one-hour intervals at standard conditions. In complex studies with ECG-monitoring, the physical load followed the recording of the hemodynamic indices.

Bicycle ergometry was carried out by the double blind method during two days, in 1.5 hour intervals after applying the film-carrier or the plate containing glycerol trinitrate onto the gum. The standard conditions of imposing dosed physical loads were observed during the tests.

On the days of studies, food and physical activity of patients were strictly controlled.

The results of studies were treated statistically by the Student's method.

Comparative pharmacodynamic studies of Sustac (6.4 and 12.8 mg) and of the antianginal plate containing glycerol trinitrate in capsules for peroral administration (6.0 and 9.0 mg) were carried out on ten patients. The materials pertaining to one patient were excluded from statistic analyses because of technical artifact of FIP. Tables 1 and 2, which follow below, give the hemodynamic indices obtained in the course of studies after taking one dose of Sustac or the antianginal plate containing glycerol trinitrate in capsules. In the group of patients who were given smaller doses (6.4 and 6.0 mg respectively), the effects differed insignificantly in both magnitude and duration.

Systolic arterial pressure (SAP) was lower compared with the initial level and remained so for three hours after taking Sustac ($7.2 \pm 1.7$ per cent maximum) and for two hours after taking the antianginal plate containing glycerol trinitrate ($8.3 \pm 3.4$ per cent maximum), but the lowered SAP was not statistically proven.

The stroke index, according to impedance cardiography, decreased distinctly in the course of the first few minutes after administrations of Sustac and remained so for 4–5 hours. The proposed antianginal plate containing glycerol trinitrate in capsules decreased the stroke index after only 30 minutes and this effect persisted for four hours. The delayed action probably depended on the time of the capsule dissolution in the alimentary tract. The maximum decrease in the stroke index was more significant after the administration of the antianginal plate containing glycerol trinitrate ($27.4 \pm 3.2$ in 60 minutes) compared with the corresponding magnitude attained after the administration of Sustac ($24.7 \pm 5.6$ in 30 minutes).

The amplitude of the wave "b", according to FIP, increased to the maximum extent in the first 10–30 minutes after the administration of Sustac and the initial level was restored in 6 hours. With the proposed antianginal plate containing glycerol trinitrate, the maximum changes were observed in longer lapses of time (in 2–3 hours) and the initial indices were restored in shorter time (by the fifth hour).

Figure 2:
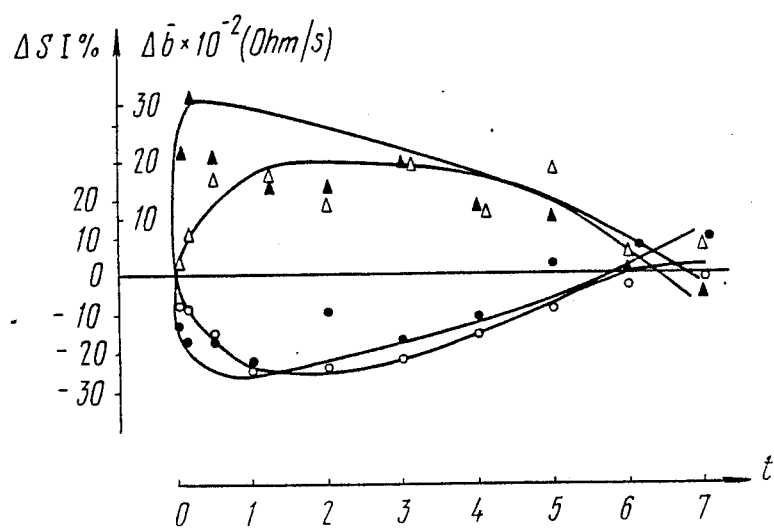

Hemodynamic indices obtained for said studies, are given in FIGS. 1 and 2. FIG. 1 illustrates pharmacodynamics of Sustac (6.4 mg) and the antianginal plate containing glycerol trinitrate (6.0 mg), taken per os, according to impedance cardiography and finger impedance ethysmography TIP. Mean data are presented. Plotted against the axis of ordinates is SI % — variations in the stroke index, in per cent of the starting value (figures to the left of the axis); $b \times 10^{-2}$ ohm/sec — the change in the value of the first negative wave "b" on the curve of the first FIP derivative, with respect to the initial value, expressed in ohm/sec with the scale factor $10^{-2}$ introduced for the sake of convenience of calculations (figures to the right of the axis). Plotted against the axis of abscissas is time (t) in hours. Circles and triangles are used for the proposed antianginal plate containing glycerol trinitrate and shaded circles and triangles for Sustac.

FIG. 2 shows pharmacodynamics of Sustac (12.8 mg) and the proposed antianginal plate containing glycerol trinitrate (9 mg), taken per os, according to impedance cardiography and FIP. Mean data are given. Symbols and designations used in the figure are the same as in FIG. 1.

The comparison shows that the hemodynamic effect of the proposed antianginal plate containing glycerol trinitrate taken per os in capsules is similar to that of the tablets of Sustac.

The pulse rate and the diastolic pressure did not significantly change except for two cases where tachycardia developed during the first 15 minutes after the administration of Sustac.

Side effects were observed in five patients after the administration of Sustac (dizziness in two and headache in three) and only in three patients (headache) after the administration of the proposed antianginal plate containing glycerol trinitrate.

Pharmacodynamics of the proposed antianginal plate containing glycerol trinitrate applied to the mouth mucosa and of glycerol trinitrate in tablets, given sublingually, were studied. The investigation showed that the time of resolution of the placeblo (the carrier plate without glycerol trinitrate) varies significantly in different persons: from 30 minutes to 6.5 hours, and in some cases even up to 10 hours. It follows therefore that one and the same antianginal plate containing, for example, 2 mg, will cause grave side effects from overdosage (hypotension, collapse, etc) in persons in whom the time of full resolution of the film is 30–45 minutes, while the same film will give insufficient dose to patients in whom the film will resolve only in six and more hours, the adequate dose of the preparation being given only to patients in whom the film will resolve in 2–3 hours.

Pharmacodynamic studies of the proposed antianginal plate containing glycerol trinitrate in doses 1, 2 and 3 mg, (depending on the time of resolution of the film tients with ischemic heart disease with angina pectoris. The plate was applied to the mouth mucosa. Glycerol trinitrate preparations did not produce any response in one patient who was therefore removed from the further analysis. The results of the studies are given in Tables 3 and 4 which follow hereinafter.

The proposed antianginal plate containing 1 mg of glycerol trinitrate was given to 9 patients wherein the plate resolved in 1.5 to 2.5 hours. Systolic arterial pressure diminished, compared with the initial level, in the course of 15 minutes following sublingual administration of glycerol trinitrate (maximum by 9.3±2.2 per cent at the fifth minute) and in the course of two hours when applying the plate on the mouth mucosa (maximum by 7.9±1.6 per cent at the 90th minute). The changes in the systolic arterial pressure were however not reliably proved statistically.

The stroke index decreased after sublingual use of glycerol trinitrate in tablets in the course of 20 minutes (maximum by 40.3±2.9 per cent by the fifth minute) and in the course of three hours with the application of the antianginal plate to the mouth mucosa (maximum by 34.9±4.1 per cent by the 60th minute).

The amplitude of the wave "b" in FIP increased to its maximum in the course of the first five minutes following sublingual use of glycerol trinitrate in tablets and restored to the initial level in thirty minutes. When the proposed plate was applied to the mouth mucosa, the amplitude of the wave "b" increased immediately and returned to the initial level in three hours.

Thus, the antianginal plate containing glycerol trinitrate produced a marked effect on the hemodynamics in the first minutes after its application to the mouth mucosa, and the effect persisted for about three hours.

TABLE 1

Dynamics of systolic arterial pressure (SAP), stroke index (SI), amplitude of wave "b" in FIP after administration of Sustac (6.4 mg) and proposed medicinal film containing glycerol trinitrate (6 mg) per os in a capsule.

| First group (n = 4) | | Mean deviation from initial level | | | | | |
|---|---|---|---|---|---|---|---|
| Sustac. 6.4 mg | Initial indices | Time after administration, min. | | | | | |
| | | 5 | 10 | 30 | 60 | 120 | 180 |
| | SAP 129.2 | −4.7 ± 2.7 | −7.2 ± 1.7 | −4.6 ± 2.2 | −8.2 ± 11.4 | −5.0 ± 2.1 | −7.0 ± 1.9 |
| | SI 26.8 | −16.3 ± 9.6 | −18.2 ± 9.4 | −24.7 ± 5.6 | −20.0 ± 5.2 | 22.7 ± 4.3$^x$ | −18.2 ± 8.6 |
| | "b" 16.2 | 8.0 ± 7.3 | 15.0 ± 10.2 | 19.0 ± 13.0 | 16 | 20.0 ± 11.4 | 15.0 ± 2.0$^{x,x}$ |
| Proposed medicinal film containing 6.0 mg of gycerol trinitrate | SAP 128.7 | −3.0 ± 7.3 | −1.5 ± 1.9 | −8.3 ± 3.4 | −3.4 ± 3.6 | 4.7 ± 2.5 | −4.4 ± 3.3 |
| | SI 29.0 | −7.5 ± 7.6 | −0.5 ± 5.2 | −10.5 ± 9.0 | −10.0 ± 3.1 | −21.7 ± 2.8$^x$ | −22.5 ± 2.9$^{x,x}$ |
| | "b" 12.5 | 12.5 ± 7.6 | 8.7 ± 3.8 | 10.0 ± 5.0 | 14.0 ± 2.4$^x$ | 24 ± 5.1$^x$ | 26.0 ± 11.5 |

| First group (n = 4) | | Mean deviation from initial level | | | | |
|---|---|---|---|---|---|---|
| Sustac. 6.4 mg | Initial indices | Time after administration, min. | | | | |
| | | 240 | 300 | 360 | 420 | 480 |
| | SAP 129.2 | −4.7 ± 3.2 | −2.1 ± 4.0 | −1.2 ± 2.8 | +0.9 ± 1.7 | +6.0 ± 2.0 |
| | SI 26.8 | −17.2 ± 4.6 | −12.7 ± 3.4 | −4.7 ± 3.0 | +3.7 ± 2.2 | +14.0 ± 1.0 |
| | "b" 16.2 | 12.5 ± 3.2$^x$ | 13.0 ± 2.8$^x$ | 9.0 ± 5.2 | −1.6 ± 1.7 | −5.0 ± 0 |
| Proposed medicinal film containing 6.0 mg of glycerol trinitrate | SAP 128.7 | −3.7 ± 5.5 | −0.9 ± 1.5 | +2.2 ± 9.8 | +1.5 ± 3.5 | −7.0 |
| | SI 29.0 | −12.7 ± 3.5 | −2.0 ± 3.6 | −4.3 ± 4.7 | +0.7 ± 3.8 | +4.0 |
| | "b" 12.5 | 29.0 ± 9.0 | 6.0 ± 5.1 | 5.0 ± 0 | 2.5 ± 2.5 | 5.0 |

Deviations in "b" are given in Ohm/sec; the other indices are in per cent; n is the number of patients:
$^x p < 0.05$;
$^{x,x} p < 0.01$ without glycerol trinitrate) were carried out on 17 pa-

TABLE 2

Dynamics of systolic arterial pressure (SAP), stroke index (SI), and amplitude of wave "b" in FIP after peroral administration of Sustac (12.8 mg) and proposed antianginal plate containing 9 mg of glycerol trinitrate per os as a capsule.

| Second group (n = 5) | Mean deviation from initial level |
|---|---|
| Sustac | Time after administration, in min. |

TABLE 2-continued

Dynamics of systolic arterial pressure (SAP), stroke index (SI), and amplitude of wave "b" in FIP after peroral administration of Sustac (12.8 mg) and proposed antianginal plate containing 9 mg of glycerol trinitrate per os as a capsule.

| 12.8 mg | Initial indices | 5 | 10 | 30 | 60 | 120 |
|---|---|---|---|---|---|---|
| | SAP 122.0 | −6.9 ± 4.1 | −7.3 ± 4.1 | −4.4 ± 4.7 | −4.8 ± 2.5 | 3.8 + 5.1 |
| | SI 31.4 | −12.6 ± 4.4$^x$ | −16.4 ± 5.1$^x$ | −15.6 ± 5.7 | −22.8 ± 2.8 | 9.2 + 4.7 |
| | "b" 19.5 | 23.0 ± 7.8 | 32.0 ± 12.4 | 21.0 ± 0.7 | 15.0 ± 6.8 | 5.0 + 9.7 |
| Proposed medicinal film containing 9 mg of glycerol trinitrate | SAP 120.6 | 0 ± 1.3 | −1.0 ± 1.9 | −3.0 ± 1.4 | −7.0 ± 2.5 | −5.1 ± 3.1 |
| | SI 31.8 | −8.6 ± 5.7 | −9.4 ± 4.6 | −16.8 ± 4.5$^x$ | −27.4 ± 3.2$^x$ | −25.0 ± 1.6$^{xxx}$ |
| | "b" 16.0 | 2.5 ± 3.2 | 8.0 ± 3.4 | 18.0 ± 5.4$^x$ | 18.0 ± 6.0$^x$ | 13.0 ± 2.0$^x$ |

| Second group (n = (n = 5) | | | | Mean deviation from initial level | | |
| Sustac | | | | Time after administration, in min. | | |
| 12.8 mg | Initial indices | 180 | 240 | 300 | 360 | 420 | 480 |
|---|---|---|---|---|---|---|---|
| | SAP 122.0 | −4.1 + 4.0 | −1.8 + 2.8 | −0.8 + 2.3 | +8.2 + 2.6 | +13.7 + 3.5 | — |
| | SI 31.4 | −17.5 + 4.3 | −11.4 + 5.6 | +13.3 + 3.8 | +5.4 + 7.8 | +8.6 + 5.0 | +7.0 |
| | "b" 19.5 | 24.0 + 10.2 | 13.6 + 6.6 | 10.0 + 6.9 | −1.1 + 3.7 | −3.6 + 5.9 | 0 + 5.0 |
| Proposed medicinal film containing 9 mg of glycerol trinitrate. | SAP 120.6 | −5.0 + 2.2 | −1.3 + 4.4 | +2.4 + 2.2 | +3.8 + 2.1 | +5.3 + 2.7 | +16.0 |
| | SI 31.8 | −23.0 + 1.9$^{xxx}$ | −16.6 + 2.1$^{xx}$ | −8.4 + 2.7 | −3.2 + 3.4 | −2.0 + 2.2 | +10.0 |
| | "b" 16.0 | 18.0 + 4.4$^x$ | 10.0 + 2.2 | 18.0 + 5.1$^x$ | 4.0 + 3.7 | 5.0 + 5.0 | 0 |

Deviations in "b" are given in Ohm/sec; the other indices are in per cent; n is the number of patients
$^x p < 0.05$;
$^{xx} p < 0.01$;
$^{xxx} p < 0.001$ The intensity of the hemodynamic effect of the antianginal plate was similar to that of glycerol trinitrate tablets given sublingually, but the intense effect persisted for much longer periods with the proposed antianginal plate.

Antianginal plate containing 2 mg of glycerol trinitrate was given to 7 patients in whom the mean resolution time of a placebo (the film carrier without glycerol trinitrate) was from 2.5 to 4 hours. The stroke index, wave "b" in FIP were proved to change and the indices were close to the data obtained with the dose of 1.0 mg. There were no reliable proofs of changes in the systolic arterial pressure. In two cases, the hemodynamic effect was observed for four hours which fully coincided with the time of resolution of the corresponding plate without glycerol trinitrate in these patients.

Figure 3:
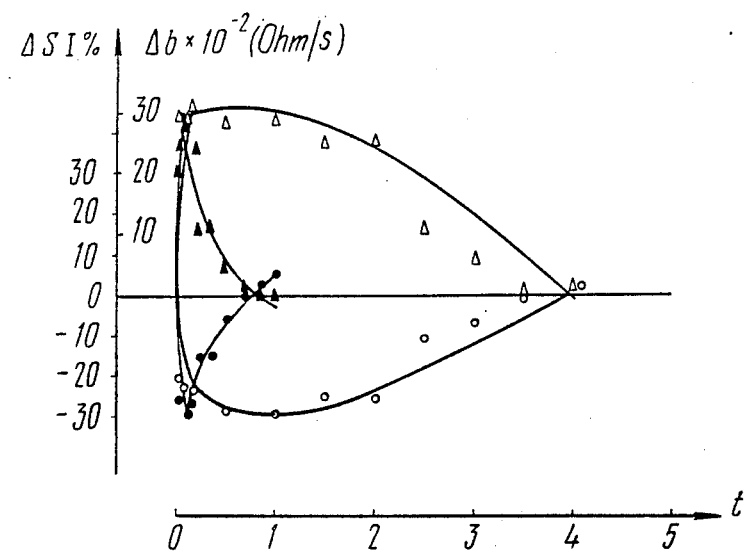
Figure 4:
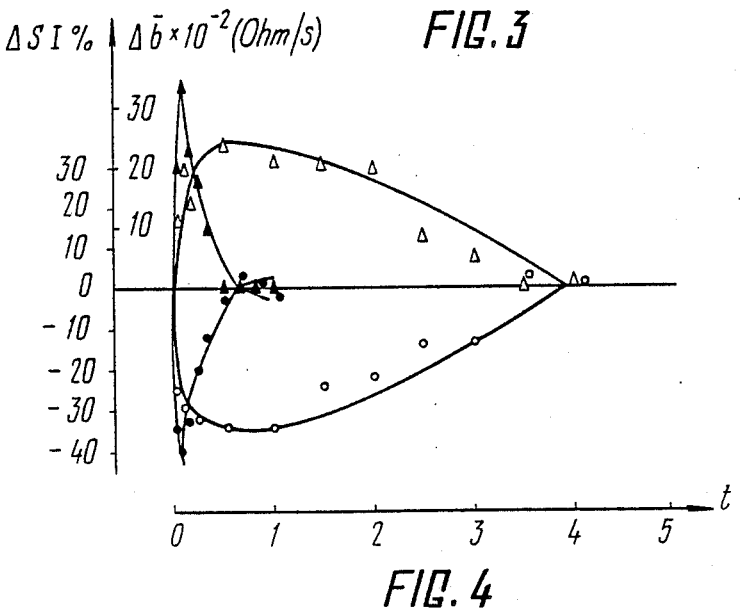

The results of said studies are given in FIGS. 3 and 4.

FIG. 3 shows pharmacodynamics of glycerol trinitrate in tablets (0.5 mg) given sublingually and the proposed antianginal plate containing glycerol trinitrate (2 mg) when applied to the mouth mucosa (according to impedance cardiography and FIP data). Mean data are given. The designations and symbols used in the figure are same as in FIG. 1.

FIG 4 shows pharmacodynamics of glycerol trinitrate tablets (0.5 mg) given sublingually and of the proposed antianginal plate containing 1 mg of glycerol trinitrate when applied to the mouth mucosa (impedance cardiography and FIP data). Mean data are given. The symbols and designations are the same as in FIG. 1.

ECG-monitoring with repeated individual selected standard physical load with treadmill was carried out as follows. Dynamics of depression of the ST segment was studied in ten patients to whom controlled physical loads were given after giving a placebo (6 patients) and the proposed antianginal plate containing 2 mg of glycerol trinitrate (8 patients). The data obtained indicate that after applying the antianginal plate containing glycerol trinitrate to the mouth mucosa, the ST segment depression (ΔD %) was reliably proved to decrease in the course of three hours under repeated individual selected standard physical loads with treadmill, the maximum effect being attained at the 30-60th minute. The ST segment depression variations in patients to whom a placebo had been given did not exceed 4 per cent. The results of the tests are given in Table 5 and FIG. 5.

Figure 5:
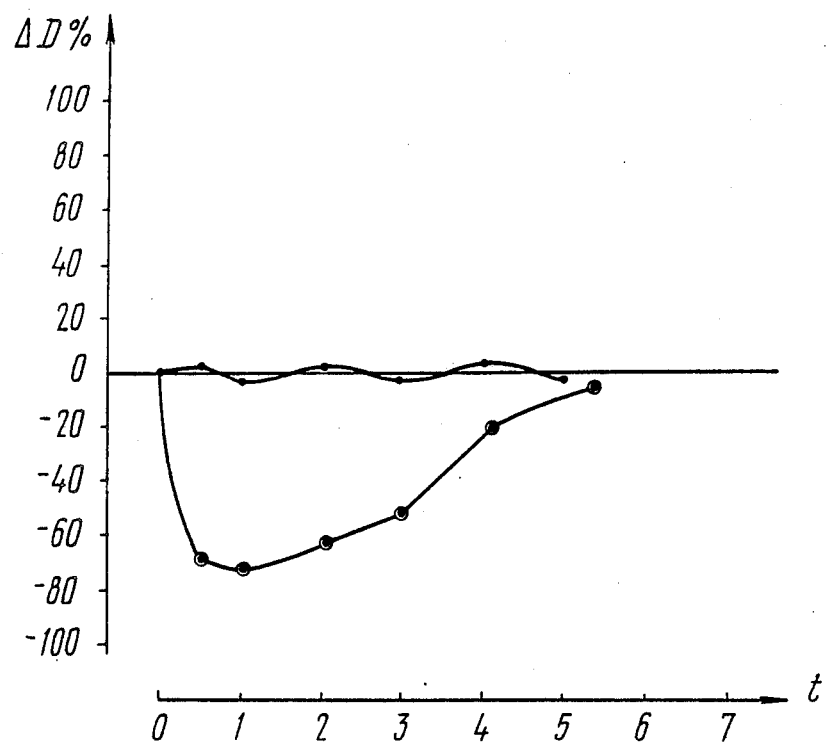

FIG. 5 shows the dynamics of the ST segment depression under repeated individual selected standard physical loads with treadmill after application of the proposed antianginal plate containing glycerol trinitrate to the mouth mucosa (2 mg), according to ECG-monitoring. Mean data are given.

Plotted against the axis of ordinates is the change in the St segment depression (ΔD %) after application of the plate without glycerol trinitrate (placebo), designated by a curve with dots; or after applying the antianginal plate containing glycerol trinitrate to the mouth mucosa (designated by a curve with dots in circles). Time (t) in minutes, after the administration of the preparation is plotted against the axis of abscissas.

Tolerance for physical load with bicycle ergometry was tested in eleven patients to whom a placebo or 1 or 2 mg of the antianginal plate containing glycerol trinitrate was given. Mean results of the bicycle ergometry test given in Table 6 show the increasing tolerance for physical load and increasing activity in patients to whom the true preparation was given. In two cases, the rising stepped load on the bicycle ergometry was stopped only because of general fatigue when the patients were given the true preparation, and the test was discontinued in all patients to whom the placebo was given (although the load was lessened) because signs of myocardial ischemia developed.

The studies carried out showed the efficacy of the proposed antianginal plate containing glycerol trinitrate both given per os (in capsules) and glued to the mouth mucosa in patients with ischemic heart disease. Comparative pharmacological studies of the antianginal plate containing glycerol trinitrate for peroral use in capsules and tablets of Sustac showed that both preparations produce similar effects on the studied hemodynamic parameters: stroke index, systolic arterial pressure, and peripheral vasodilation. Objective hemodynamic measurements showed that the antianginal plate containing glycerol trinitrate, given per os in capsules, produces a specific pharmacodynamic effect in the course of 4-4.5 hours (like Sustac). When considering mean data, important information concerning individual response to the therapy should also be included. For example, the indices were quite varied after the administration of 12.8 mg of Sustac, which as associated with individual response of patients to the preparation.

More uniform results were obtained with the proposed antianginal plate containing glycerol trinitrate applied to the mouth mucosa of the patients. The direct uptake of glycerol trinitrate by the body, bypassing the liver, ensures a pronounced pharmacodynamic effect of the plate applied to the mouth mucosa which manifests practically instantaneously and persists for 2.5-4 hours. This method of administration of the active principle has the following advantages: a reliable and pronounced hemodynamic effect is attained with markedly lower doses of the active substance; patients do not complain of any inconveniences and tolerate this medicinal form well; a great advantage of the new form is that it is possible to control the uptake of glycerol trinitrate whenever necessary; it is easy to discontinue the uptake of the preparation by removing the unresolved plate in cases where it becomes necessary, or, on the contrary, it is easy the renew the therapy, the therepautic effect being attained practically instantaneously.

TABLE 3

Dynamics of systolic arterial pressure (SAP), Stroke index (SI), and amplitude of wave "b" after application of antianginal plate containing glycerol trinitrate to mouth mucosa

| | Initial indices | Mean deviations from initial level in minutes | | | | |
| --- | --- | --- | --- | --- | --- | --- |
| | | 2 | 5 | 10 | 30 | 60 |
| Group 1 (n= 9) plate containing 1 mg | SAP 134.3 | $-2.7 \pm 0.6$ | $-2.8 \pm 0.7$ | $-4.2 \pm 1.3$ | $-7.3 \pm 0.8$ | $-7.8 \pm 1.6$ |
| | SI 28.8 | $-25.0 \pm 5.5^{xx}$ | $-27.8 \pm 4.1^{xxx}$ | $-32.2 \pm 3.5^{xxx}$ | $-33.6 \pm 3.1^{xxx}$ | $-34.9 \pm 4.1^{xxx}$ |
| | "b"14.2 | $13.1 \pm 4.0^{x}$ | $20.3 \pm 4.6^{xx}$ | $15.3 \pm 3.0^{xxx}$ | $24.2 \pm 4.8^{x}$ | $22.2 \pm 5.9^{xx}$ |
| Group 2 (n= 7) plate containing 2 mg of glycerol trinitrate | SAP 125.3 | $-3.1 \pm 1.2$ | $6.2 \pm 1.3$ | $-5.0 \pm 3.8$ | $-5.9 \pm 1.0$ | $-5.4 \pm 1.6$ |
| | SI 27.9 | $-21.0 \pm 1.2^{xxx}$ | $-23.2 \pm 3.8^{xx}$ | $-23.4 \pm 2.8^{xxx}$ | $-28.3 \pm 6.1^{xx}$ | $-28.9 \pm 5.6^{xx}$ |
| | "b"0.15 | $28.9 \pm 6.0^{xx}$ | $28.3 \pm 4.4^{xxx}$ | $31.4 \pm 4.3^{xxx}$ | $28.6 \pm 4.4^{xx}$ | $29.3 \pm 3.0^{xx}$ |

| | Initial indices | Mean deviations from initial level in minutes | | | | |
| --- | --- | --- | --- | --- | --- | --- |
| | | 90 | 120 | 150 | 180 | 210 | 240 |
| Group 1 (n= 9) plate containing 1 mg | SAP 134.3 | $-7.9 \pm 1.6$ | $-3.8 \pm 0.8$ | $-0.5 \pm 1.0$ | $-0.3 \pm 1.2$ | $+1.2 \pm 2.0$ | $+2.2 \pm 1.6$ |
| | SI 28.8 | $-25.4 \pm 5.0^{xx}$ | $-23.3 \pm 4.6^{xx}$ | $-14.2 \pm 5.7$ | $-14.3 \pm 5.1$ | $+3.2 \pm 1.8$ | $+1.0 \pm 4.4$ |
| | "b"14.2 | $20.0 \pm 7.6^{x}$ | $20.6 \pm 7.09^{xx}$ | $7.5 \pm 2.8$ | $5.0 \pm 2.4$ | $0 \pm 1.4$ | $1.5 \pm 4.1$ |
| Group 2 (n= 7) plate containing 2 mg of glycerol trinitrate | SAP 125.3 | $-6.0 \pm 1.5$ | $-5.4 \pm 1.3$ | $-5.1 \pm 1.9$ | $-0.6 \pm 0.8$ | $+2.6 \pm 1.7$ | $+2.6 \pm 1.8$ |
| | SI 27.9 | $-27.06 \pm 6.2^{x}$ | $-26.4 \pm 7.0^{x}$ | $-19.4 \pm 3.9^{x}$ | $-12.3 \pm 4.4$ | $-3.7 \pm 5.2$ | $-3.4 \pm 5.6$ |
| | "b"0.15 | $25.5 \pm 7.3^{x}$ | $25.8 \pm 8.1$ | $11.0 \pm 1.0^{x}$ | $7.1 \pm 2.6$ | $0 \pm 2.9$ | $2.0 \pm 2.0$ |

Notes:
deviations in "b" are given in Ohm/sec; the other indices are in per cent;
$^{x}p < 0.05$;
$^{xx}p < 0.01$;
$^{xxx}p < 0.001$
n is the number of patients

TABLE 4

Dynamics of systolic arterial pressure (SAP), stroke index (SI), and wave "b" amplitude in TRP after sublingual administration of glycerol trinitrate tablet (0.5 mg)

| | Tablets of glycerol trinitrate. 0.5 mg Initial indices | Mean deviation from initial level Time after administration, min. | | | |
| --- | --- | --- | --- | --- | --- |
| | | 2 | 5 | 10 | 15 |
| Group 1 (n = 9) | SAP 130.8 | $-7.1 \pm 1.5$ | $-8.3 \pm 2.2$ | $-4.2 \pm 1.6$ | $-2.7 \pm 1.7$ |
| | SI 28.8 | $-34.3 \pm 4.6^{xxx}$ | $-40.3 \pm 2.9$ | $-33.8 \pm 4.3^{xxx}$ | $-20.0 + 3.9^{xx}$ |
| | "b"18.6 | $21.0 \pm 5.8^{x}$ | $34.0 \pm 8.2^{xx}$ | $24.0 \pm 5.9^{xx}$ | $18.0 \pm 4.6^{xx}$ |
| Group 2 (n = 7) | SAP 129.3 | $-8.7 \pm 2.6$ | $-9.6 \pm 2.1$ | $-7.9 \pm 1.8$ | $-3.5 \pm 3.3$ |
| | SI 30.5 | $-26.3 \pm 6^{xx}$ | $-29.6 \pm 5.4^{xx}$ | $-28.4 \pm 5.7^{xx}$ | $-16.1 \pm 7.7$ |
| | "b"16.0 | $20.0 \pm 5.3^{x}$ | $28.0 \pm 5.4^{xx}$ | $22.0 \pm 4.3^{xx}$ | $11.0 \pm 5.5$ |

| | Tablets of glycerol trinitrate. 0.5 mg Initial indices | Mean deviation from initial level Time after administration min. | | | | |
| --- | --- | --- | --- | --- | --- | --- |
| | | 20 | 30 | 40 | 50 | 60 |
| Group 1 (n = 9) | SAP 130.8 | $+0.8 \pm 2.1$ | $+0.4 \pm 1.1$ | $+2.1 \pm 1.1$ | $+2.3 \pm 0.2$ | $+3.0 \pm 1.0$ |
| | SI 28.8 | $-12.0 \pm 4.0$ | $-3.1 \pm 2.0$ | $+3.7 \pm 2.4$ | $+1.0 \pm 4.2$ | $-2.3 \pm 5.0$ |
| | "b"18.6 | $10.0 \pm 3.0^{x}$ | $0 \pm 3.0$ | $0 \pm 1.7$ | $0 \pm 2.0$ | $0 \pm 5.0$ |
| Group 2 (n = 7) | SAP 129.3 | $-6.1 \pm 3.4$ | $-3.7 \pm 4.1$ | $+0.6 \pm 3.3$ | $-1.7 \pm 2.7$ | $-2 \pm 0$ |
| | SI 30.5 | $-16.1 \pm 3.9^{x}$ | $-6.0 \pm 3.9$ | $+0.3 \pm 3.5$ | $+2.2 \pm 3.9$ | $+4.7 \pm 5.9$ |

TABLE 4-continued

Dynamics of systolic arterial pressure (SAP), stroke index (SI), and wave "b" amplitude in TRP after sublingual administration of glycerol trinitrate tablet (0.5 mg)

| "b" 16.0 | $12.0 \pm 3.5^x$ | $5 \pm 2.5$ | $2.0 \pm 0.9$ | $0 \pm 1.6$ | $0 \pm 1.7$ |

Deviations in "b" are given in Ohm/sec; the other indices are given in per cent; n is the number of patients;
$^x p < 0.05$;
$^{xx} p < 0.01$;
$^{xxx} p < 0.001$

TABLE 5

Pharmacodynamics of antianginal plate containing 2 mg glycerol trinitrate when applied to mouth mucosa (mean data of the repeated individual selected standard physical loads with treadmill in combination with ECG-monitoring)

| | | Time after Administration, min. | | | | | | |
|---|---|---|---|---|---|---|---|---|
| | | 0 | 30 | 60 | 120 | 180 | 240 | 300 |
| Placebo (n = 6) | $P_{max}$(st/min) | $88.5 \pm 3.2$ | $94.0 \pm 3.5$ | $90.5 \pm 4.2$ | $86.6 \pm 4.6$ | $87.8 \pm 3.9$ | $86.6 \pm 3.4$ | $90.5 \pm 4.6$ |
| | $ST_{max}$ (mm) | $1.3 \pm 0.3$ | $1.2 \pm 0.1$ | $1.2 \pm 0.1$ | $1.2 \pm 0.2$ | $1.3 \pm 0.2$ | $1.3 \pm 0.2$ | $1.2 \pm 0.2$ |
| | D (u) | $4.2 \pm 0.9$ | $3.3 \pm 0.5$ | $3.6 \pm 0.6$ | $4.7 \pm 1.1$ | $4.2 + 1.1$ | $4.2 \pm 0.9$ | $3.6 \pm 0.6$ |
| | D (%) | 0 | $3.6 \pm 5.6$ | $-1.0 \pm 3.8$ | $0.1 \pm 3.0$ | $-0.4 \pm 3.4$ | $2.8 \pm 3.0$ | $-1.4 \pm 4.2$ |
| Medicinal film containing glycerol trinitrate (n = 8) | $P_{max}$(st/min) | $101.8 \pm 3.3$ | $1000.1 \pm 2.6$ | $95.1 \pm 2.4$ | $95.5 \pm 2.1$ | $97.4 \pm 3.6$ | $99.5 \pm 3.8$ | $107.2 \pm 6.3$ |
| | $ST_{max}$ (mm) | $1.9 \pm 0.31$ | $0.6 \pm 0.22$ | $0.4 \pm 0.13$ | $0.7 \pm 0.17$ | $1.0 \pm 0.3$ | $1.6 \pm 0.35$ | $2.0 \pm 0.2$ |
| | D (u) | $6.6 \pm 0.97$ | $2.1 \pm 0.70$ | $1.9 \pm 0.66$ | $2.7 \pm 0.7$ | $3.6 \pm 1.00$ | $5.7 \pm 1.3$ | $5.8 \pm 0.9$ |
| | D (%) | 0 | $-70 \pm 7.2^{xx}$ | $-74.0 \pm 6.8^{xx}$ | $-62.7 \pm]7.9^{xx}$ | $-52.6 \pm 11.2^x$ | $-19.7 \pm 7.1$ | $-4.5 \pm 7.8$ |

$P_{max}$ is the maximum pulse rate under load;
$ST_{max}$ is the maximum depression depth of segment ST under load;
D is the ST-segment normative depression
$^x p < 0.01$;
$^{xx} p < 0.001$;
n is the number of patients

TABLE 6

Comparison of ECG data taken under controlled physical load on bicycles ergometry after giving placebo and antianginal plate containing 1 or 2 mg of glycerol trinintrate (applied to mouth mucosa of the upper gum)

| | Mean load | | Load intensity, kg-m per min | Time of continuous work, min | Heart Beat rate | | Arterial pressure | | Criteria for discontinuation of test | |
|---|---|---|---|---|---|---|---|---|---|---|
| n = 11 | kg-m | % | | | initial | under load | initial | under load | AP + ST ↓ | dyspnea |
| Placebo | 2154 | 100 | 395.4 | 6.6 | 72.3 | 119.8 | 126/78 | 167/97 | 11 | 0 |
| Medicinal film containing glycerol trinitrate | 4425 | 240 | 600.0 | 10.4 | 82.5 | 131.0 | 115/78 | 160/91 | 9 | 2 |

AP means of angina pectoris
ST ↓ is segment ST depressions ≧ 1 mm;
n is the number of patients The high efficacy of the proposed antianginal plate has been proved by the data of the test with physical loads which showed considerable improvement of tolerance for load and increased activity of patients with the antianginal plate attached to the mouth mucosa.

Hemodynamic data well agree with the results of ECG-monitoring under repeated individual selected standard physical loads, which objectively proves efficacy of the proposed plate containing glycerol trinitrate.

Side effects, which develop during the treatment with the proposed plate containing glycerol trinitrate, are insignificant. Slight plucking at the site of application of the plate was reported by 11 patients in the course of the first 10-30 minutes, after which these sensations subside. Nine patients had dizziness, the same as with the use of glycerol trinitrate tablets for sublingual administration.

Individual doses of antianginal plate containing other active principles, e.g. isosorbide dinitrate, pentaerythritol tetranitrate, etc., can also be given for application to the mouth mucosa with equivalent results.

The method of individual dosage ensures not only a more prolonged effect of the preparation (in the course of a few hours) but also diminishes side effects such as headache, dizziness, postural hypotonia, and nausea. It is known that like glycerol trinitrate, isosorbide dinitrate taken per os in the form of tablets is rapidly metabolized in the liver by the enzymatic mechanism, i.e. its bioavailability with the administration per os is low and differs significantly in various patients. If isosorbide dinitrate is used in the antianginal plate as the active substance, it enters the blood circulating system from the mouth mucosa bypassing the liver.

When isosorbide dinitrate or pentaerythritol tetranitrate tablets are taken per os the major part of the active principle gets into the blood circulating system in inactivated form because of its metabolism in the liver.

The method of individual doses of the antianginal plates containing isosoribide dinitrate or pentaerythritol tetranitrate ensures the delivery of the active substance into the systemic blood circulation bypassing the liver. Using the aforementioned active principles considerably prolong the hemodynamic effect (in the course of several hours) and diminishes side effects, such as headache, noise in the ears, dizziness, postural hypotension, diarrhea.

An important advantage of the proposed medicinal plate possessing antianginal action is its high adhesion in the swollen state to the mouth mucosa which makes it possible to attach it to a chosen site of the mucosa where it remains fixed until fully resolved to ensure uniform delivery of the active substance directly into the mucosa and further into the blood circulation system bypassing the gastrointestinal tract to rule out uncontrolled partial inactivation of the active principle.

In contrast to the known carriers, polymer carriers of the proposed antianginal plate on contact with aqueous solutions, ensure markedly more uniform delivery of the active substance into the body which decreases, side effects such as headache, or sharp changes in blood pressure which are otherwise observed with the known antianginal preparations. The uniform liberation of the active principle, for example, of glycerol trinitrate, from the antianginal plate is illustrated in Table 7 which is given below (the data are given in comparison with the known tablets of glycerol trinitrate).

The method of preparing the antianginal plate according to the invention is as follows: Solutions of a biologically resolvable soluble polymer carrier and the active substance are prepared in standard mixers. The solvents should be compatible, or a single solvent should be used to dissolve the active substance and the polymer carrier. The solutions are then put together at the required ratio of the components, air is removed from the solutions in vacuum at room temperature and a film, 0.1 to 1.5 mm thick, is cast on an inert surface by using standard casting equipment. The film is dried at temperatures to 40° C. until the residual amount of the solvent does not exceed 10 per cent by weight, and oval plates of the required size are pressed out mechanically. If the medicinal film should contain dispersed fat, it is introduced into the solution containing the active substance and the biologically soluble and resolvable polymer carrier, and the mixture is stirred mechanically, by ultrasound, or by any other known method to ensure uniform distribution of fat in the mixture.

The thus prepared antianginal medicinal plates having prolonged action and improved accuracy of dosage, can be stored for periods of time that considerably exceed expiration time of other medicinal forms such as dragees, tablets, granules, etc.

For a better understanding of the invention, the following examples of its practical embodiment are given by way of illustration.

TABLE 7

Liberation of the glycerol trinitrate from different medicinal forms of introglycerin

| Antianginal preparation | Amount of the active substance (in %) liberated in time lapses (min) | | | | |
|---|---|---|---|---|---|
| | 2 | 5 | 10 | 30 | 60 |
| Glycerol trinitrate tablets | 40 | 70 | 100 | — | — |
| Medicinal plate of polyacrylamide containing glycerol trinitrate | 20 | 35 | 60 | 80 | 100 |
| Medicinal plate of copolymer of acrylamide, vinylpyrrolidone and ethyl acrylate (1:1:1) containing glycerol trinitrate | 25 | 40 | 60 | 75 | 100 |

EXAMPLE 1

Antianginal plate having the following composition, in per cent by weight, is prepared:

| | |
|---|---|
| glycerol trinitrate | 3 |
| polyacrylamide (molecular mass, 970,000) | 97 |

A solution of glycerol trinitrate ethyl alcohol, having a concentration of 1 per cent by weight, and polyacrylamide solution in water, having a concentration of 10 per cent are prepared in glass vessels. Next, 970 g of polyacrylamide solution are placed in a vessel provided with a stirrer and 30 g of glycerol trinitrate solution are added. Stirring is continued for 30 minutes at 80-100 rpm. The solution is then placed in a vacuum cabinet and air is removed from the solution at 10 mm Hg for 2-3 hours at room temperature. The solution is not cast onto a polished metal plate in a 4-5 mm thick layer. The plate is placed in a heated cabinet and kept there for 24 hours at a temperature of 20° C., then for 12 hours at a temperature of 30° C., and finally for 12 hours at 40° C. The obtained medicinal film, 0.5 mm thick, is kept at room temperature for 24 hours, and oval plate, 7 mm in diameter, are stamped out mechanically. Each plate contains about 0.5 mg of glycerol trinitrate.

EXAMPLE 2

Antianginal plate containing the following components, in per cent by weight, is prepared:

| | |
|---|---|
| glycerol trinitrate | 30 |
| copolymer of acrylamide, N-vinylpyrrolidone, and ethylacrylate (1:1:1; mol. weight, 80,000) | 70 |

The components are dissolved in an aqueous-alcohol mixture (75:25) to obtain 10-20 per cent solutions. The medicinal plate is then prepared by the procedure described in Example 1.

EXAMPLE 3

Antianginal plate having the following composition, in per cent by weight, is prepared:

| | |
|---|---|
| glycerol trinitrate | 10 |
| copolymer of acrylamide, N-vinylpyrrolidone and butyl-acrylate (1:0.5:3; mol. weight, 80,000) | 90 |

The components are subsequently dissolved in an aqueous-alcohol mixture (75:25) to obtain 10-20 per cent solutions. The further procedure is the same as described in Example 1.

EXAMPLE 4

Antianginal plate having the following composition, in per cent by weight, is prepared:

| | | |
|---|---|---|
| glycerol trinitrate | 3 | |
| copolymer of acrylamide, N-vinylpyrrolidone and ethylacrylate (0.6:0.2:0.2; mol. wt., 50,000) | 97 | |
| cocoa butter | 3 | (with respect to the other components) |

The components are subsequently dissolved and dispersed in an aqueous-alcohol mixture (75:25) to obtain 10-20 per cent solutions and dispersions of the components. The dispersion is prepared by mechanical stirring. The further procedure is the same as described in Example 1.

EXAMPLE 5

Antianginal plate, having the following composition, in per cent by weight, is prepared:

| | | |
|---|---|---|
| glycerol trinitrate | 5 | |
| copolymer of acrylamide, N-vinylpyrrolidone, and ethylacrylate (0.6:0.2:0.2; mol. wt., 500,000) | 95 | |
| cocoa butter | 30 | (with respect to all other components) |

The further procedure for preparing the plate is the same as described in Example 4.

EXAMPLE 6

Antianginal plate, having the following composition, in per cent by weight, is prepared:

| | | |
|---|---|---|
| glycerol trinitrate | 5 | |
| copolymer of acrylamide, N-vinylpyrrolidone and ethyl acrylate (0.6:0.2:0.2; mol. weight, 500,000) | 95 | |
| hydrogenized cotton-seed oil | 10 | (with respect to all other components) |

The method of preparing the plate is described in Example 4.

EXAMPLE 7

Antianginal plate, having the following composition, in per cent by weight, is prepared:

| | | |
|---|---|---|
| pentaerythritol tetranitrate | 20 | |
| copolymer of acrylamide, N-vinylpyrrolidone and ethylacrylate (0.6:0.2:0.2; mol. wt., 500,000) | 80 | |
| cocoa butter | 10 | (with respect to all other components) |

The procedure for preparing the medicinal plate is the same as described in Example 4.

EXAMPLE 8

Antianginal plate, having the following composition, in per cent by weight, is prepared:

| | |
|---|---|
| isosorbide dinitrate | 20 |
| copolymer of acrylamide, N-vinylpyrrolidone and ethylacrylate (0.6:0.2:0.2; mol. wt., 500,000) | 80 |

The components are subsequently dissolved in an aqueous-alcohol mixture (50:50) to obtain 15-20 per cent solutions of the components. The further procedure is the same as described in Example 1.

EXAMPLE 9

Antianginal plate having the following composition, in per cent by weight, is prepared:

| | | |
|---|---|---|
| pentaerythritol tetranitrate | 20 | |
| copolymer of acrylamide, N-vinylpyrrolidone and ethyl acrylamide (0.6:0.2:0.2; mol. wt. 500,000) | 80 | |
| cocoa butter | 10 | (with respect to all other components). |

The method is the same as described in Example 4.

EXAMPLE 10

Antianginal plate having the following composition, in per ent by weight, is prepared:

| | | |
|---|---|---|
| glycerol trinitrate | 5 | |
| polyvinylpyrrolidone (mol. wt., 40,000) | 95 | |
| glycerol laurate | 10 | (with respect to all other components) |

The method for preparing the medicinal plate is the same as described in Example 4.

EXAMPLE 11

Antianginal plate, having the following composition, in per cent by weight, is prepared:

| | | |
|---|---|---|
| glycerol trinitrate | 5 | |
| copolymer of an acrylamide, N-vinyl-pyrrolidone and ethyl acrylate (0.6:0.2:0.2; mol wt., 500,000) | 95 | |
| glycerol phthalate | 10 | (with respect to all other components) |

The method for preparing the medicinal plate is the same as described in Example 4.

The advantages of the method of the present invention are confirmed by clinical tests in comparison with prior art methods and medications as shown in the following Examples:

EXAMPLE 12:

Comparison of the Arresting Antianginal Effect of Trinitrolong Plates Applied on the Upper Gum and Nitroglycerin Tablets for Sublingual Application by Patients with Angina Pectoris of Effort The study was carried out on nine patients with ischemic heart disease exhibiting a typical angina pectoris of effort. Initially, all the patients were subjected to a continuously rising stepped load on a bicycle ergometry according to the standard protocol. All the specially selected patients showed, under the ergometry load, a depression of the ST segment in the leads $V_{3-6}$ of the horizontal or down-sloping type to at least 1.5 mm. at a distance of 0.08 sec. from the point j, accompanied by a typical attack of angina pectoris. Tolerance to physical load was low (60 W, or less) in three patients, and medium 90 to 120 W) in six patients. Under every load, a patient developed a typical attack of angina pectoris and ischemic changes in the ECG. The duration of the anginal attack was measured by a stopwatch. The ECG (in leads $V_{3-6}$) and arterial pressure were recorded at the end of every minute. The maximum heart rate during anginal attack developing under the control bicycle ergometry load was in the range of 110 to 128 beats per minute for different patients. The duration of physical load at the control period was from 90 to 120 sec.

On the day of the tests, the patients were given three bicycle ergometry loads at an interval of at least 4 hours.

The first control load the patient was taken off the load as an anginal attack developed and ischemic changes were observed in the ECG but glycerol trinitrate wasn't given to assess usual duration of the anginal attack.

The second load: the load was relieved at the onset of an anginal attack and the patient was simultaneously given a 0.5 mg nitroglycerin tablet sublingually.

The third load: identical to the previous two, but in this case a plate of trinitrolong medication was applied in front to the mucosa of the upper gum over the canine teeth or premolars.

Trinitrolong is the new antianginal product in plate form containing a coronary vasodilator nitrate, in a non-toxic, biodegradable, mouth mucosa-soluble polymer, and when affixed to a chosen site of the mouth mucosa remains highly adhered and releases the active principle immediately, thereafter at a sustained high concentration, and wherein the bioavailability of the active principle is greater than that obtained when using sublingual nitroglycerin tablets. Preferred polymers are the homopolymers of acrylamide and vinylpyrrolidone and their copolymers with acrylates.

There was a good replication of bicycle ergometry loads until ischemic signs developed in the ECG and an anginal attack set in. The duration of the anginal attack was $119.0 \pm 18.7$ sec after the first control load, and considerably less than $-91.3 \pm 15.7$ (p 0.01) and $89.3 \pm 14.8$ (p 0.01) sec., respectively—after the second load (following in the application of nitroglycerin sublingually) and the third load (following the application of trinitrolong on the upper gum). There was no difference in the duration of the second and third loads. Therefore, nitroglycerin tablets taken sublingually and trinitrolong plates applied to the mucosa of the upper gum equally reliably reduced the duration of an anginal attack induced by bicycle ergometry. The medications had a similar effect on the dynamics of the ST segment depression at the termination of loads.

Some experiments used a continuous load method, i.e., with the first signs of an anginal attack following bicycle ergometry control loads, the patient was given a 0.5 mg nitroglycerin tablet sublingually, or a 2 mg Trinitrolong plate was applied to the upper gum mucosa, with the bicycle ergometry load continuing.

According to the continuous physical load method, with the onset of an anginal attack and depression of the ST segment, the patient felt the attack abating 30 sec after taking a nitroglycerin tablet sublingually and 32 sec after application of a Trinitrolong plate to the upper gum mucosa. The anginal attack was fully arrested under continuing load 1 min. 10 sec and 1 min. 15 sec. after the application of these two medications, respectively. Simultaneously, the ST segment was observed to rapidly return to the isoline despite the continuing physical load.

Therefore, 0.5 mg. nitroglycerin tablets taken sublingually and 2 mg. plates of the claimed medication applied to the upper gum musoca were equally effective in arresting attacks of angina pectoris accompanied by ischemic changes in the ECG (depression of the ST segment).

EXAMPLE 13

Investigation of the Arresting Effect of Three Medicinal Forms of Glycerol Trinitrate The capacity of a nitroglycerin tablet, taken sublingually in a 0.5 mg dose, a Trinitrolong plate in a 2 mg dose, and a buccal tablet of Susadrin in a 1 mg dose (both applied on the upper gum) to arrest an anginal attack was studied in eight patients with ischemic heart disease, showing a stable angina of effort of 2nd and 3rd functional classes. The study was conducted by treadmill load trials. Initially, a treadmill load, which caused an onset of anginal attack of two points (++) for 4 to 6 mins., was chosen for each patient. The same individually selected loads were then used at which the arresting effect of the above-mentioned medications was studied. As the first signs (to +) of angina pectoris developed under load, a patient was given one of the medications studied and the load was continued until the anginal attack was arrested or pain developed to ++ (the medication was ineffective).

Nitroglycerin in tablet sublingually arrested the beginning anginal attack in 6 out of 8 patients. In two patients, the anginal attack could not be arrested with the help of nitroglycerin in tablet sublingually although one of these patients also took a double dose of nitroglycerin tablets, 1 mg., sublingually. The desired effect could not be achieved in either of these two patients with Trinitrolong and Susadrin. Trinitrolong arrested an anginal attack in 5 out of 8 patients, but in one patient responsive to nitroglycerin tablets sublingually, Trinitrolong could not arrest the anginal attack (Trinitrolong was tested twice for this patient but in neither case was the desired effect produced). Susadrin was only effective for one patient, who was also responsive to nitroglycerin and trinitrolong.

|  | Number of patients responsive to | | |
| --- | --- | --- | --- |
|  | Nitroglycerin | Trinitrolong | Susadrin |
| Effect present | 6 | 5 | 1 |
| No effect | 2 | 3 | 7 |

An arresting effect of a buccal tablet of Susadrin was therefore observed in only one out of eight patients, whereas nitroglycerin tablets sublingually and Trinitrolong plates applied on the upper gum according to the present method were equally effective in the majority of patients studied.

EXAMPLE 14:

Comparison of Pharmacokinetics of Trinitrolong, Nirtoderm, Susadrin and Sustac in Single Doses of Medications Studied Trinitrolong (3 mg in the form of plates to be applied to the upper gum mucosa)

Two minutes after application, nitroglycerin concentrations in the plasma reach a significant value—an average of 0.86±0.36 ng/ml, and remain at this level for 3 hours, never dropping below 0.84±0.15 ng/ml. The maximum concentraton was reached 2 hours after use, 1.15±0.24 ng/ml. The dissolution time of the plate (3.8±0.3 hrs.). By the fifth hour, the concentration was equal to 0.10±0.03 ng/ml.

Susadrin (1 mg in buccal tablet form)

It is detected in the blood in 2 min., but at a significantly lower concentration than in the case of Trinitrolong plate, namely: 0.41±0.04 ng/ml. if 0.5 ng/ml were considered as the lowest therapeutical level for nitroglycerin, the concentration is below this level in all instances involving Susadrin. When, however, Trinitrolong was used, the concentration was above 0.5 ng/ml in 46% of the cases, which means that it can be used for arresting attacks of angina pectoris. The maximum concentration achieved by Susadrin was observed 2 hours after use, 0.63±0.15 ng/ml, after which it declined slowly, reaching 0.35±0.10 ng/ml by the third hour, and 0.19±0.07 ng/ml by the fifth hour. On the whole, all concentrations lay below the concentrations obtained by Trinitrolong. Whereas individual concentrations between the 10th minute and 3 hours after application of Trinitrolong lie essentially in the region above 0.5 ng/ml (only 19% of the values lie below, 5% being attributed to the fast dissolution of the plate, and in 8% the values were recorded in a patient showing low concentrations within the entire range studied), in the case of the buccal tablet of Susadrin, 54% of the values lie in the region below 0.50 ng/ml.

Nitroderm (50 mg in the form of patches discs applied to skin)

The concentration grows gradually, reaching a mere 0.30±0.11 ng/ml after 0.5 hour. Two hours after application, a maximum of 1.05±0.27 ng/ml was observed. After 6 hours, the concentration dropped to 0.51±0.12 ng/ml, and did not rise above this level until the 24th hour. After 24 hours, the average concentration was 0.39±0.07 ng/ml. A considerable difference was observed in data from patient to patient. Besides, significant fluctuations of concentration were observed in the same patient. In the period up to the 3rd hour, concentrations below 0.5 ng/ml were observed in 37% of the individual values within 10 hours, in 50%, and within 24 hours, in 52% of the individual values. As in the case of Susadrin the concentration for nitroderm was in many instances below the therapeutical level in the course of investigations.

Sustac (6.4 mg in the form of peroral tablets)

With Sustac administered to patients, in two out of four instances, nitroglycerin was not detected in blood throughout the observation period. In the remaining instances, nitroglycerin concentrations were very low. The maximal concentration was 0.21±0.13 ng/ml but usually not exceeding 0.1 ng/ml.—approximately 10%.

From the viewpoint of bioavailability, time of detection in blood in sufficient concentrations, and constant therapeutical level in the blood that does not drop below 0.5 ng/ml, Trinitrolong has an unquestionable advantage over the other medicinal forms of glycerol trinitrate. It must be emphasized especially that it is convenient in use.

TABLE 8

Pharmacokinetic parameters of glycerol trinitrate from different medicinal forms (± standard average error)

| Medicinal form | Medication, dose | Number of patients | Dissolution time | $C_{max}$ ng/ml | $T_{max}$ | Bioavailability (in %) |
|---|---|---|---|---|---|---|
| Sublingual tablets | Nitroglycerin, 0.5 mg | 30 | 51 ± 6 sec | 3.37 ± 0.48 | 4.4 ± 0.2 min | 100 |
| Plates | Trinitrolong, 3 mg | 13 | 3.8 ± 0.3 hrs | 1.76 ± 0.35 | 1.5 ± 0.3 hrs | 217 ± 58 |
| Patches | Nitroderm 50 mg | 6 | — | 1.18 ± 0.22 | 3.5 ± 1.3 hrs | 31 ± 7 |
| Buccal tablets | Susadrin 1 mg | 4 | 3.6 ± 1.0 | 0.73 ± 0.09 | 1.5 ± 0.5 hrs | 231 ± 8 |
| Peroral tablets | Sustac 6.4 mg | 4 | — | 0.21 ± 0.13 | 2.5 ± 1.5 hrs | 10 |

EXAMPLE 15

Comparison of the Pharmacodynamic Effect of the Transdermal Form of Nitroglycerin and Trinitrolong Plates Applied to Gum Mucosa The efficiency of nitroglycerin in two medicinal forms, transdermal (nitroderm patches) and medicinal plates for application to the upper gum mucosa (Trinitrolong) was studied on nine patients with ischemic heart disease. The duration and degree of the anti-ischemic effect were assessed with the help of individual repeated selected standard loads with treadmill performed prior to and many times 0.5, 2, 3, 5, 6, 8 and 24 hours after application of the medications.

Besides, in the case of nitroderm patches, similar loads were repeated at 8.5 and 24.5 hours after taking 0.5 mg nitroglycerin sublingually (after 5 min.).

The effect of a placebo, 3 mg Trinitrolong and 50 mg nitroderm (in one patient and 100 mg) was studied in all the patients on different days. The anti-ischemic effect was assessed from the reduction of the maximum depression of the ST segment during each individual selected standard load with treadmill after drug administration compared with the level of the ST segment depression attained under control load on the day of study prior to drug administration, and was expressed in percentage points. The anti-ischemic effect of nitroderm patches (discs) was detected only 0.5 to 3 hours after application of the medication to the skin, reaching a maximum in 7.9±2.1 hours. The maximum effect was expressed considerably lower for nitroderm patches (65±6%) than for sublingual nitroglycerin tablets (78±5%) and Trinitrolong plates (80±6%). The average duration of the effect was 7.9±2.1 hours for nitroderm patches and 4.6±0.6 hours for Trinitrolong plates. Individual analysis of data showed that the effect of nitroderm was first recorded 0.5 hours after application in 4 patients; 1 hour in one patient, 2 hours in three patients, and 3 hours in one patient.

The expressed effect of Trinitrolong was recorded in this study in all the nine patients at the first measurement (i.e., after 0.5 hours).

The data of clinical tests including comparative pharmacodynamic and pharmacokinetic studies, as set forth above, support the substantial distinctions and advantages of the claimed method for treating patients suffering from ischemic heart disease.

What is claimed is:

1. A method for treating ischemic heart disease in a patient subject to anginal pectoris comprising the step of adhering to a chosen site of the mouth mucosa an antianginal film composition in plate form useful for treating ischemic heart diseases in patients subject to anginal pectoris and which is capable of adherence to a selected site of the mouth mucosa for rapid arresting or prevention of anginal pectoris attacks whereby said composition when highly adhered remains fixed and glued to a chosen site of the mouth mucosa and insures immediate, uniform and sustained delivery of an antianginal nitrate, in an amount effective for an average of about 5 hours per plate, directly into the blood circulation system through the mouth mucosa, with the great advantage that it is possible to control and easily discontinue the nitrate uptake by removing the unresolved film in cases where it becomes necessary or, on the contrary, to renew the therapy, said antianginal composition comprising from about 3 to 30 weight percent of an antianginal nitrate in a complex labile bond with from about 70 to 97 weight percent of a mouth mucosa soluble, swellable and resolvable polymeric film-forming carrier, in which solutions of the biologically resolvable soluble polymer carrier and the active substance were mixed, and a film cast and dried until the residual amount of the solvent does not exceed about 10 percent by weight;

said film-forming carrier having the ability to:
(a) form labile complex bonds with said anti-anginal coronary vasodilating nitrate;
(b) remain highly adhered to the mouth mucosa, but can be removed to interrupt or discontinue treatment; and
(c) release the active principle of said coronary vasodilator nitrate immediately, and thereafter at such a sustained rate and for a period of time that the pharmacodynamic effects as expressed by the mean data of the repeated individual selected standard physical loads with treadmill in combination with ECG-monitoring
  (i) are detectable practically instantaneously after affixing to the mouth mucosa,
  (ii) confirm the presence of a continuous therapeutic concentration of said active principle in the patient's blood during resolution of said carrier, and
  (iii) confirm a bioavailability of said active principle in an amount substantially greater than that obtained with a sublingual nitroglycerin tablet as the standard.

2. The method of claim 1 wherein said antianginal nitrate is selected from the group consisting of glycerol trinitrate, pentaerythritol tetranitrate, and isosorbide dinitrate.

3. The method of claim 1 wherein from about 3 to about 30% by weight of a dispersed solid fat melting at temperatures of from 30° to 50° C. is present based on the total weight of said nitrate and carrier.

4. The method of claim 3 where said solid fat is selected from the group consisting of cocoa butter, hydrogenized cotton seed oil, glycerol laurate, and glycerol phthalate.

5. The method of claim 1 wherein said polymer carrier has the ability to form labile complex bonds with said antianginal coronary vasodilating nitrates, said nitrates having been prepared by mixing solvent solutions of said labile complex bond-forming polymer and said antianginal nitrate, removing air from the solution in vacuum at room temperature, casting a film and drying the film at temperatures up to 40° C.

6. The method of claim 1 wherein said film is from about 0.1 to about 1.5 mm thick.

7. A method for treating ischemic heart disease in a patient subject to anginal pectoris comprising the step of adhering to a chosen site of the mouth mucosa and antianginal film composition in plate form useful for treating ischemic heart diseases in patients subject to anginal pectoris and which is capable of adherence to a selected site of the mouth mucosa for rapid arresting or prevention of anginal pectoris attacks whereby said composition when highly adhered remains fixed and glued to a chosen site of the mouth mucosa and insures immediate, uniform and sustained delivery of an antianginal nitrate directly into the blood circulation system through the mouth mucosa, in an effective sustained amount for an average of about 5 hours per plate, and with the great advantage that it is possible to control and easily discontinue the nitrate uptake by removing the unresolved film in cases where it becomes necessary or, on the contrary, to renew the therapy, said antianginal composition comprising from about 3 to 30 weight percent of an antianginal nitrate in a complex labile bond with from about 70 to 97 weight percent of a mouth mucosa soluble, swellable and resolveable polymer film-forming carrier selected from the group consisting of homopolymers of acrylamide and vinylpyrrolidone and their copolymers with acrylates, in which solutions of the biologically resolvable soluble polymer carrier and the active substance were mixed, and a film cast and dried until the residual amount of the solvent does not exceed about 10 percent by weight;

said film-forming carrier having the ability to:
(a) form labile complex bonds with said anti-anginal coronary vasodilating nitrate;
(b) remain highly adhered to the mouth mucosa, but can be removed to interrupt or discontinue treatment, and
(c) release the active principle of said coronary vasodilator nitrate immediately, and thereafter at such a sustained rate and for a period of time that the pharmacodynamic effects as expressed by the mean data of the repeated individual selected standard physical loads with treadmill in combination ECG-monitoring
  (i) are detectable practically instantaneously after affixing to the mouth mucosa, (ii) confirm the presence of a continuous therapeutic concentration of said active principle in the patient's blood during resolution of said carrier, and
(iii) confirm a bioavailability of said active principle in an amount substantially greater than that obtained with a sublingual nitroglycerin tablet as the standard.

* * * * *